United States Patent
Kühn et al.

(10) Patent No.: US 8,574,214 B2
(45) Date of Patent: Nov. 5, 2013

(54) CARTRIDGE AND NEEDLE SYSTEM THEREFOR

(75) Inventors: Bernd Kühn, Frankfurt am Main (DE); Hermann Koch, Mainz (DE); Christopher James Smith, Frankfurt am Main (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 53 days.

(21) Appl. No.: 13/056,160

(22) PCT Filed: Aug. 17, 2009

(86) PCT No.: PCT/EP2009/005940
§ 371 (c)(1),
(2), (4) Date: Jun. 3, 2011

(87) PCT Pub. No.: WO2010/022870
PCT Pub. Date: Mar. 4, 2010

(65) Prior Publication Data
US 2011/0224640 A1    Sep. 15, 2011

(30) Foreign Application Priority Data

Aug. 30, 2008 (EP) .................................. 08015367

(51) Int. Cl.
*A61J 1/06* (2006.01)
*A61M 5/28* (2006.01)
(52) U.S. Cl.
USPC ............ 604/415; 604/411; 604/412; 604/413
(58) Field of Classification Search
USPC ........................ 604/542, 403–416
See application file for complete search history.

(56) References Cited

U.S. PATENT DOCUMENTS

| 4,226,236 | A | * | 10/1980 | Genese ........................ 604/89 |
| 5,435,076 | A | * | 7/1995 | Hjertman et al. ............... 34/296 |
| 5,549,561 | A |   | 8/1996 | Hjertman |
| 5,554,134 | A | * | 9/1996 | Bonnichsen .................. 604/240 |
| 5,611,785 | A |   | 3/1997 | Mito et al. |
| 5,803,284 | A | * | 9/1998 | Grimard ...................... 215/249 |
| 5,895,383 | A | * | 4/1999 | Niedospial, Jr. .............. 604/403 |
| 2004/0059312 | A1 | * | 3/2004 | Frezza et al. ................. 604/411 |
| 2007/0102393 | A1 | * | 5/2007 | Colin et al. .................. 215/249 |

FOREIGN PATENT DOCUMENTS

| DE | 2900827 | 7/1980 |
| DE | 19537163 | 1/1997 |
| EP | 0261318 | 3/1988 |

(Continued)

OTHER PUBLICATIONS

International Search Report for corresponding International App. No. PCT/EP2009/005940, dated Dec. 4, 2009.

(Continued)

*Primary Examiner* — Philip R Wiest
*Assistant Examiner* — Benjamin Klein
(74) *Attorney, Agent, or Firm* — McDonnell Boehnen Hulbert & Berghoff LLP

(57) ABSTRACT

The invention refers to a cartridge (100), such as an injection cartridge, and to a needle system (200) therefore. Further, the invention refers to a combination of such an injection cartridge and a needle system. More specifically, the invention refers to a closure system for an injection cartridge which allows attachment of a needle system to the cartridge.

20 Claims, 24 Drawing Sheets

(56) References Cited

FOREIGN PATENT DOCUMENTS

| GB | 705392   | 3/1954  |
|----|----------|---------|
| GB | 1151222  | 5/1969  |
| WO | 84/02079 | 6/1984  |
| WO | 96/30065 | 10/1996 |

OTHER PUBLICATIONS

European Search Report for priority patent application EP App. No. 08015367, dated Feb. 3, 2009.
International Preliminary Report on Patentability for International App. No. PCT/EP2009/005940, dated Mar. 1, 2011.

* cited by examiner

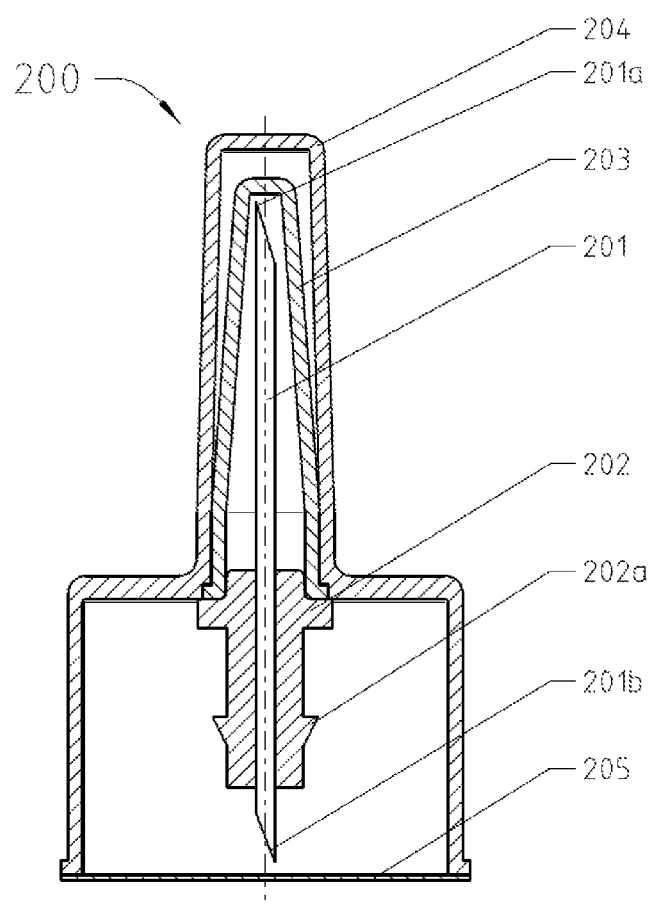

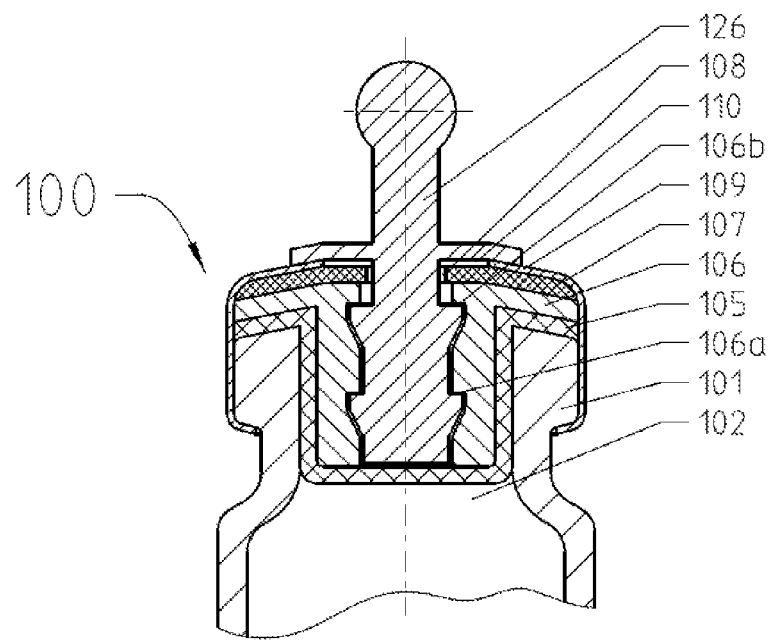

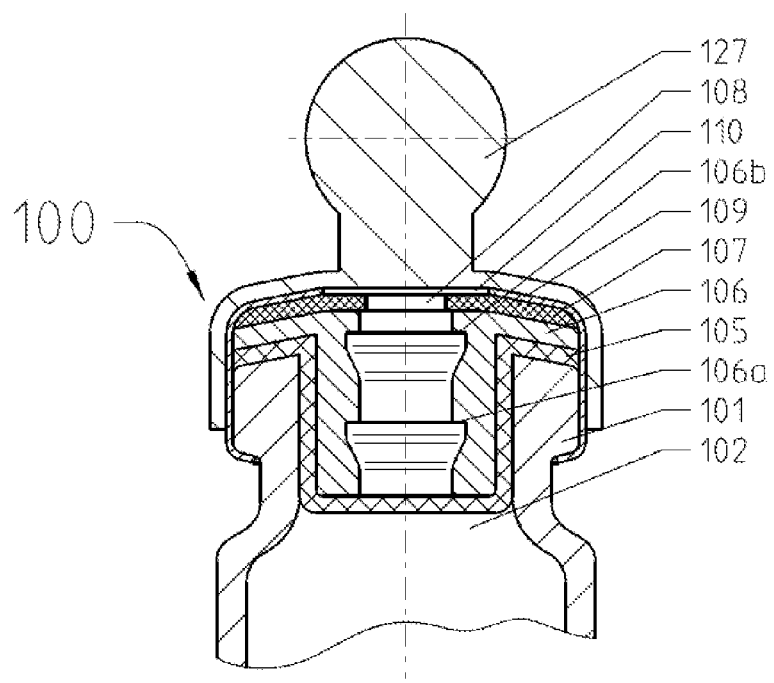

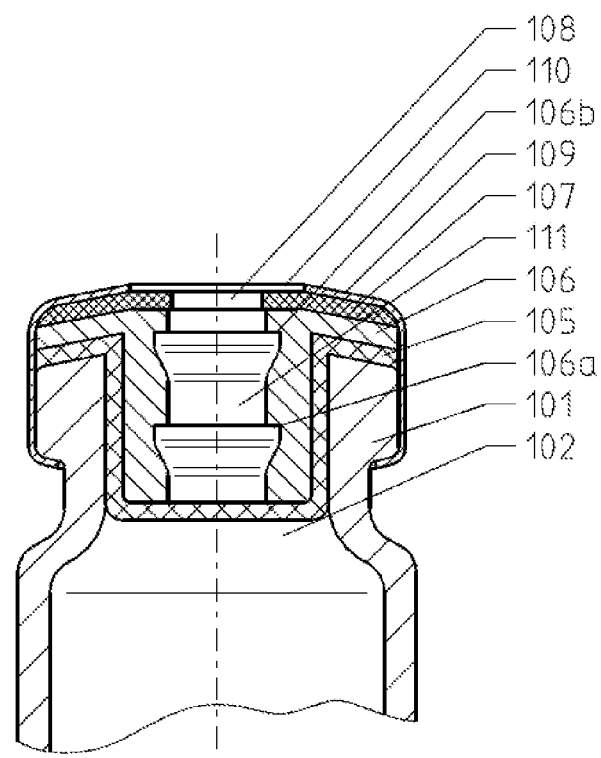

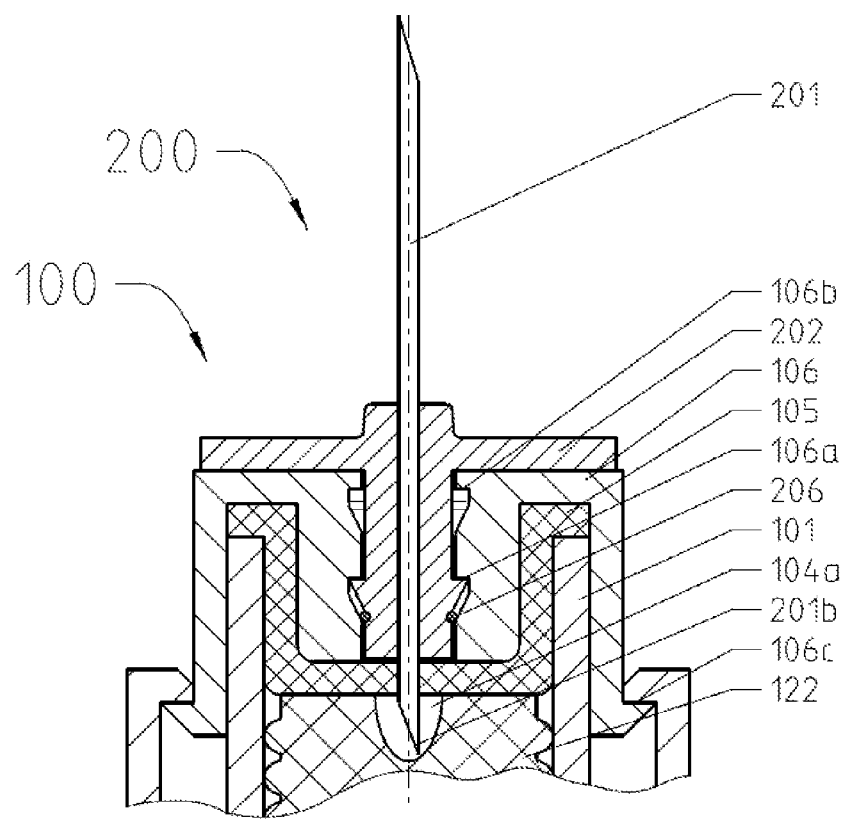

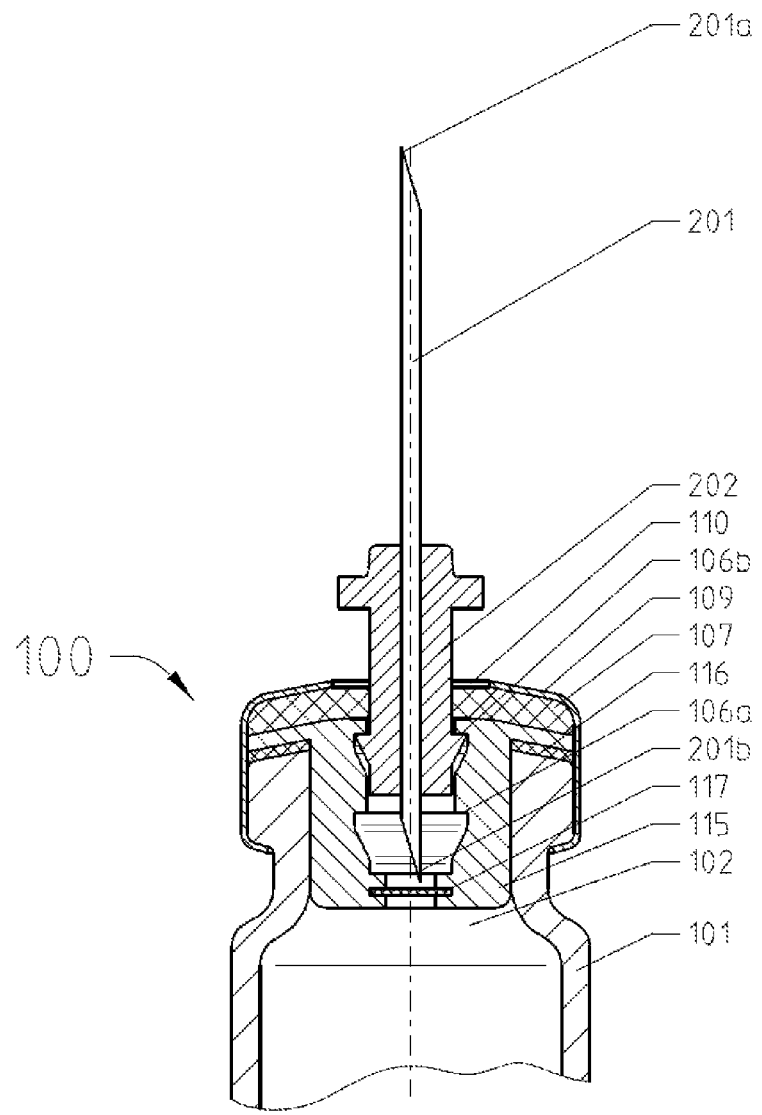

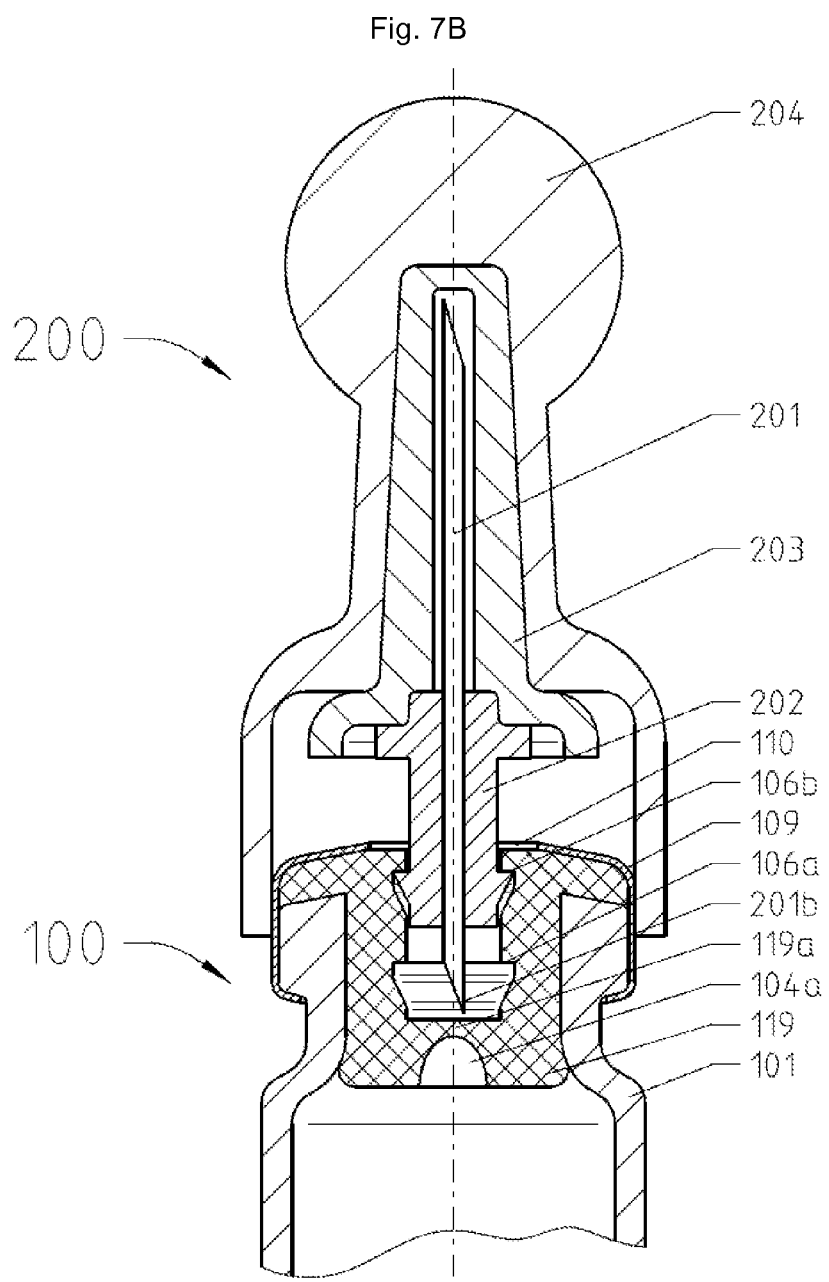

CARTRIDGE AND NEEDLE SYSTEM THEREFOR

CROSS REFERENCE TO RELATED APPLICATIONS

The present application is a U.S. National Phase Application pursuant to 35 U.S.C. §371 of International Application No. PCT/EP2009/005940 filed Aug. 17, 2009, which claims priority to European Patent Application No. 08015367.9 filed on Aug. 30, 2008. The entire disclosure content of these applications are herewith incorporated by reference into the present application.

FIELD OF THE INVENTION

The invention refers to a cartridge, such as an injection cartridge, and to a needle system therefor. Further, the invention refers to a combination of such an injection cartridge and a needle system. More specifically, the invention refers to a closure system for an injection cartridge which allows attachment of a needle system to the cartridge.

BACKGROUND

U.S. Pat. No. 5,549,561 and U.S. Pat. No. 5,435,076 show injection cartridges of the dual-chamber type comprising a barrel with a distal end and a proximal end. In the barrel, there is provided a proximal piston which is displaceable within the barrel. A further displaceable piston is provided in the distal direction of the proximal piston to define a first chamber between the two pistons. The distal end of the barrel is closed by a rubber septum which is held in place with a metal crimp.

The needles for use with such a cartridge usually consist of a needle with an attached hub. The needle hub fits around the outside of the cartridge closure and carries features to attach the needle to the cartridge or to an injection device, for example a screw thread. Such needles are typically supplied as a separate component to the injection device and are attached manually by the user prior to injection. The needles are supplied with a plastic outer cover which can be used to provide a means for handling the needle and for protecting the user from potential needle stick injuries.

The injection cartridge of U.S. Pat. No. 5,549,561 or U.S. Pat. No. 5,435,076 has a distal end which is configured as a neck with a reduced inner diameter. This neck allows fastening of the metal crimp. Needles typically used for such a cartridge have a distal tip and a proximal tip, the latter penetrating the rubber septum when attaching the needle to the cartridge. Thus, the proximal tip of the needle protrudes into the neck of the injection cartridge. This typically leaves a dead space in the neck of the cartridge. This is a volume of a cartridge from which the contents cannot be accessed where a quantity of drug product can remain after administration.

The dead space creates a number of disadvantages. Additional medicament may need to be filled to compensate for dead space losses. This is generally not desired and is a commercial disadvantage, especially for expensive products. Also, in applications where the entire content of the cartridge is dispensed any variability of the dead space volume will have a direct impact on the accuracy of the delivered dose.

The problem of dead space is particularly relevant for delivery of suspensions because it may cause the suspension to become inhomogeneously mixed. For example the dead space known from U.S. Pat. No. 5,549,561 or U.S. Pat. No. 5,435,076 may preferentially trap solid particles (or microspheres) because it is also an area of relatively slow or stationary fluid flow.

There are two reasons why this dead space is present. Firstly, the design of the device, needle and cartridge closure must ensure that the needle will always pierce the septum, irrespective of manufacturing tolerances. Secondly, the design of the device, needle and piston in the cartridge must ensure that the piston never hits the needle tip.

Current needles are designed such that the needle protrudes some way past the septum and into the cartridge as shown in U.S. Pat. No. 5,435,076 or GB 705,392. This is to take account of various manufacturing and assembly tolerances that could affect whether or not the needle pierces the septum. For example, needle length, septum thickness, screw thread tolerances on needle hub and medical device, crimping strength, glass cartridge dimensions, degree to which the user tightens the needle on the screw thread etc.

GB 705,392 discloses a syringe having at its distal end a sleeve-like stopper with a rubber septum integrally formed in this stopper. A needle may be attached to this syringe such that the proximal tip of the needle pierces the rubber septum. Again, the stopper defines a dead space for receiving the proximal tip of the needle.

EP 0 261 318 A1 describes an injection device with a cartridge which has a distal end and which is closed by a rubber member. Within the distal end of the cartridge, a needle is provided which may be forwarded to pierce the rubber element and to protrude from the distal end of the cartridge as a piston is forwarded within the cartridge. This configuration of the cartridge and the needle again creates a relatively large dead space in the distal end of the cartridge.

Further, WO 84/02079 A1 refers to a cartridge having at its distal end a cartridge closure in the form of a cap enclosing the distal end of the cartridge. A central distal portion of this cap is configured as a hollow tip protruding in the distal direction of the cartridge. This hollow tip is closed by a septum which is integrally formed with the cap and the tip. Opening of this known cartridge may be achieved by pushing a short needle with a single, proximal tip in the protruding tip of the cap thus piercing the septum so that the needle tip protrudes into the distal end of the cartridge. As the distal end of the cartridge is formed with a neck with a reduced inner diameter, again a dead space is created.

In addition to the drawbacks of a dead space, known cartridges face the risk of bending of the needle piercing the septum outside the center and piercing into side-walls of the closure inside the cartridge which may damage or block the needle. This risk of an improper alignment of the needle with respect to the septum is caused by the fact that the needle usually is not guided with respect to the septum.

SUMMARY

In view of the foregoing, it is a principle object of the present invention to provide an injection cartridge and a needle system which reduce the dead space in the distal end of the cartridge. It is a further object of the present invention to reduce the risks of bending of the needle, piercing the septum outside the center or piercing into the side-walls of the closure inside the cartridge.

According to the present invention, this is achieved essentially by an injection cartridge comprising a barrel having a distal end and a proximal end and a housing insert, wherein the housing insert is at least partially received in the distal end of the barrel and wherein the housing insert comprises a central opening for at least partially receiving a plug-like member having a hub or shaft with said central opening comprising retaining means for guiding and retaining the hub and being aligned to attachment means of the hub. In other words, the retaining means in the central opening allows the housing insert to receive the hub of the plug-like member in such a manner that the plug-like member is held in a correct position within the central opening of the housing insert and that the hub is held in place within the housing insert such that additional means for attaching the plug-like member to the cartridge may be omitted.

The housing insert may be any suitable device allowing to be at least partially inserted into the distal end or the neck portion of the cartridge. It is preferred that the housing insert, if applicable together with sealing means, is held in the distal end of the injection cartridge in fluid-tight manner. Further, advantageously, the housing insert extends into the distal end of the cartridge such that a piston abuts the housing insert if the barrel is empty or at least comes in the vicinity of the housing insert.

The plug-like member may be any suitable device which may be at least partially inserted with its hub or shaft into the central opening of the housing insert. As an example, the plug-like member may be a needle system or a closure plug. The central opening is configured with its retaining means such that the hub of the plug-like member together with its attachment means is guided within the housing insert such that a needle or the like is in a defined position with respect to the septum, which position is preferably, to align the needle with the longitudinal axis of the cartridge. Further, the plug-like member is held within the housing insert such that the plug-like member may not become detached from the housing insert and the cartridge in use.

In a preferred embodiment of the invention, the central opening of the housing insert has a cylindrical inner surface for guiding a cylindrical outer surface of the hub of the plug-like member. Alternatively, the central opening of the housing insert has a conical inner surface for guiding a conical outer surface of the hub of the plug-like member. In this alternative, conical preferably means a deviation of up to 5 degree, more preferred 0.5-2 degree from the axis of the housing.

In another preferred embodiment of the injection cartridge, the central opening of the housing insert has an inner surface and the hub of the plug-like member has an outer surface with at least one protrusion being provided on one of said inner or outer surfaces and at least one recess being provided on the other of said inner or outer surfaces for retaining the plug-like member in the housing insert.

In a more specific embodiment of the injection cartridge according to the invention, there are provided two recesses in one of said inner or outer surfaces which are spaced apart in an axial (longitudinal) direction of the barrel for retaining the plug-like member into two different axial positions in the housing insert. It is preferred to have these two recesses being provided in the inner surface of the central opening of the housing with the plug-like member having on its outer surface one flange-like protrusion. The protrusion may have a distal surface extending radially with respect to the longitudinal axis of the cartridge and a proximal surface which is slanted with respect to the distal surface. In addition, the recesses in the housing insert may have a distal surface extending radially from the said axis of the cartridge. Thus, the protrusion and the recesses form a snap fit connection.

According to a preferred embodiment of the invention, the central opening of the housing is a through-hole being provided with closing means for blocking a fluid communication between the barrel and the central opening.

In a more specific embodiment of the instant invention, the closing means comprises a separate stopper member, semipermeable membrane attached to the housing insert or a septum being integrally formed with the housing insert.

In a further preferred embodiment, the plug-like member is a needle system comprising a needle with a distal tip, a proximal tip and a hub or shaft surrounding the needle preferably near its proximal tip. As an alternative, the plug-like member may be a removable tamper-proofed plug for closing the injection cartridge prior to its first use. Such a plug may be used for closing the injection cartridge after the first use, too.

Thus, the proposed invention reduces the number of factors that can affect the needle protrusion depth. According to the invention the needle hub or shaft may be overmoulded to the needle and in the cartridge closure the housing insert (neck-insert) and the closing means, like a septum, are preferably in contact with one another. The housing insert having retaining means carries features that control the depth to which the needle hub having attachment means can be inserted and assures correct needle placement.

As state of the art, product loss can be reduced by filling the dead space of the cartridge neck with intruding parts of the closure as shown in U.S. Pat. No. 5,435,076. Risks of the current closure designs are related to bending of the needle, piercing the septum outside the center, and piercing into side-walls of the closure inside the cartridge which may damage or block the needle. By the proposed invention, the internal part of the needle is minimized in length to only pierce the septum. This reduces the risk of the needle bending and the needle can also be accurately aligned and centered by molded lead-ins on the needle hub and closure housing insert (neck-insert). A further advantage of shorter needles is that they have lower resistance of the fluid pathway and reduce the required forces for administration of the product.

Where injection needles have to be adapted to the cartridge system, a needle hub is normally placed on top or around the diameter of the cartridge as a protruding part, either increasing the total length of the system or the external diameter or both. This is shown for example in U.S. Pat. No. 5,435,076. However, this configuration has a particular disadvantage for the wide-necked cartridge design where further increases to the length or external diameter of the cartridge and needle system may make the cartridge incompatible with an injection device or require significant increases in the size of the device. It is a further advantage of the present invention that the additional length or diameter of the cartridge is minimized by using the space inside the neck of the cartridge to perform the needle alignment and attachment functions.

In a preferred embodiment of the injection cartridge, the distal end of the barrel is closed by a stopper member and the proximal end of the barrel is closed by a piston displaceable in said barrel such that the barrel, the stopper member and the piston define at least one chamber containing at least one product. Alternatively, in another preferred embodiment of the invention, the barrel is a dual-chamber container with the distal end of the barrel being closed by a stopper member, the proximal end of the barrel being closed by a proximal piston displaceable in said barrel and with a further displaceable piston being provided between the stopper member and the first piston such that the barrel, the stopper member and the pistons define two chambers each containing at least one product. In a more particular embodiment, the barrel is provided with a bypass being arranged such that a first product being received in a first chamber is allowed to flow into the second chamber bypassing the further piston.

According to the invention, it is preferred that in a piston, in the housing insert and/or in a stopper member there is provided a needle cavity for receiving a proximal tip of a needle system This needle cavity is preferably the only dead space remaining in the cartridge. The needle cavity allows the proximal tip of the needle system to protrude into the barrel without coming into contact with a piston. It is preferred to have the volume of the needle cavity reduced to a minimum.

Optionally, the housing insert and/or a stopper member has a cup-like configuration and is provided with a radial flange covering the distal front wall of the barrel. Thus, the housing insert and/or the stopper member fulfill the function of a sealing disc. In a more specific embodiment, the housing insert is provided with a flange having a sleeve-like section encompassing the distal end of the barrel wherein the sleeve-like section has at least one radial protrusion for fixing the cartridge in a container or device. This allows a very reliable and easy attachment of the cartridge with the aid of the flange of the housing insert and/or the stopper member. The sleeve-like section can be formed as a 360 degree surrounding sleeve. Alternatively, the sleeve-like section can be formed as a 360 degree surrounding sleeve having intersections. Thereby the sleeve is reduced to "hooked arms". In this alternative, the sleeve consists of at least 1 hooked arm, typically 2 or 3 hooked arms.

According to a further aspect of the present invention, a needle system is provided which is especially suitable for an injection cartridge as described above. The inventive needle system comprises a needle with a distal tip, a proximal tip and a hub or shaft surrounding the needle preferably near its proximal tip wherein the hub is provided with attachment means for guiding and retaining the hub in an injection cartridge, preferably in a housing insert of an injection cartridge. Prior art needle systems usually have a hub which is designed for attachment to the barrel of the injection cartridge or to an injection device. Thus, the needle is aligned with respect to the barrel of the injection cartridge or to the injection device and not with respect to the septum or the like closing member which has to be pierced by the proximal tip of the needle. This gives rise to risks like bending of the needle, piercing the septum outside the center or piercing into side-walls of the closure. In contrast to that, the needle system according to the present invention is provided with attachment means for guiding and retaining the hub with respect to an injection cartridge, in particular to a housing insert (neck insert) of the injection cartridge which is in closed contact to the septum or which has the septum as an integral part thereof. Thus, the risks of an improper piercing or bending of the needle is reduced to a minimum.

In a more specific embodiment of the present invention, the attachment means comprises at least one flange-like protrusion provided on a cylindrical outer surface of the hub. Thus, the needle is designed with self-alignment features to avoid failures as piercing the septum at an incorrect position or incorrect angle or bending the needle.

According to a further aspect of the present invention, a combination of an injection cartridge as described above and a needle system as described above is provided with the configuration of the central opening of the housing insert of the cartridge and the configuration of the hub or shaft of the needle system being adapted to each other such that the needle of the needle system is centered and guided to lie essentially within the longitudinal axis of the barrel.

Thus, the combination of a medicament cartridge closure system and a needle system minimises dead space volume in the cartridge and minimises the overall length and diameter of the injection device incorporating this cartridge once the needle has been attached. The needles for use with such cartridges currently consist of a needle with an attached hub or shaft. In contrast, prior art needle systems have a hub that fits around the outside of the cartridge closure and carries features to attach the needle to the cartridge or injection device, for example a screw thread. The combination of the present invention features a housing insert (neck-insert) which is recessed into the neck of the cartridge thus minimizing internal dead volume. This housing insert carries features designed to accept a specific design of needle hub which also fits inside the neck of the cartridge, i.e. the distal end of a barrel. By avoiding protruding needle hubs the total length and/or external diameter of the injection device can be minimized.

The needle system having self-alignment features on the needle hub, the outer needle cover, the housing insert (neck-insert) and/or the injection device can be supplied separately. As an alternative, the injection cartridge is provided with an integrated injection needle assembled into the housing insert. Preferably, the integrated needle is assembled in a position where the septum sealing the cartridge is not pierced. Prior to use the user performs some action to cause the proximal end of the integrated needle to pierce the septum. This action could be performed "automatically" as part of one of the other handling steps of the injection device, for example removing the sterile seal covering the distal end of needle, pressing the injection device against the skin or delivering the injection. Such an integrated needle and automatic septum-piercing mechanism is more convenient for the user and also reduces or eliminates the risk of associated handling errors.

In general, the invention is directed to a closure system to be put in place onto the primary package, i.e. the cartridge system, during the manufacturing step of a drug product. The cartridge according to the invention and its closure is especially useful with a "wide-necked" cartridge for integration into an autoinjector device. In this case, the wide neck is necessary to enable filling of a powder material through the neck opening of a dual-chamber cartridge in a high speed filling line. However, the inventive principle can also be applied to any medicament cartridge for use with manual or automatic injection devices.

The term "medicament" as used herein means a pharmaceutically active compound having a molecular weight up to 1500 Da, or a pharmaceutically active peptide, protein, DNA, RNA, antibody, enzyme, hormone or oligonucleotide, or a mixture thereof, or a pharmaceutical formulation comprising one or more of the afore-mentioned pharmaceutically active ingredients, preferably comprising at least one peptide, further preferred a peptide for the treatment of diabetes mellitus or complications associated with diabetes mellitus such as diabetic retinopathy, especially preferred human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N- palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 preferably means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-$NH_2$.

Exendin-4 derivatives are for example selected from the following list of compounds:

H-$(Lys)_4$-des $Pro^{36}$, des $Pro^{37}$ Exendin-4(1-39)-$NH_2$,
H-$(Lys)_5$-des $Pro^{36}$, des $Pro^{37}$ Exendin-4(1-39)-$NH_2$,
des $Pro^{36}$ [$Asp^{28}$] Exendin-4(1-39),
des $Pro^{36}$ [$IsoAsp^{28}$] Exendin-4(1-39),
des $Pro^{36}$ [$Met(O)^{14}$, $Asp^{28}$] Exendin-4(1-39),
des $Pro^{36}$ [$Met(O)^{14}$, $IsoAsp^{28}$] Exendin-4(1-39),
des $Pro^{36}$ [$Trp(O_2)^{25}$, $Asp^{28}$] Exendin-4(1-39),
des $Pro^{36}$ [$Trp(O_2)^{25}$, $IsoAsp^{28}$] Exendin-4(1-39),
des $Pro^{36}$ [$Met(O)^{14}$ $Trp(O_2)^{25}$, $Asp^{28}$] Exendin-4(1-39),
des $Pro^{36}$ [$Met(O)^{14}$ $Trp(O_2)^{25}$, $IsoAsp^{28}$] Exendin-4(1-39); or
des $Pro^{36}$ [$Asp^{28}$] Exendin-4(1-39),
des $Pro^{36}$ [$IsoAsp^{28}$] Exendin-4(1-39),
des $Pro^{36}$ [$Met(O)^{14}$, $Asp^{28}$] Exendin-4(1-39),
des $Pro^{36}$ [$Met(O)^{14}$, $IsoAsp^{28}$] Exendin-4(1-39),
des $Pro^{36}$ [$Trp(O_2)^{25}$, $Asp^{28}$] Exendin-4(1-39),
des $Pro^{36}$ [$Trp(O_2)^{25}$, $IsoAsp^{28}$] Exendin-4(1-39),
des $Pro^{36}$ [$Met(O)^{14}$ $Trp(O_2)^{25}$, $Asp^{28}$] Exendin-4(1-39),
des $Pro^{36}$ [$Met(O)^{14}$ $Trp(O_2)^{25}$, $IsoAsp^{28}$] Exendin-4(1-39), wherein the group -$Lys_6$-$NH_2$ may be bound to the C-terminus of the Exendin-4 derivative;

or an Exendin-4 derivative of the sequence

H-$(Lys)_6$-des $Pro^{36}$ [$Asp^{28}$] Exendin-4(1-39)-$Lys_6$-$NH_2$,
des $Asp^{28}$ $Pro^{36}$, $Pro^{37}$, Pro38Exendin-4(1-39)-$NH_2$,
H-$(Lys)_6$-des $Pro^{36}$, $Pro^{38}$ [$Asp^{28}$] Exendin-4(1-39)-$NH_2$,
H-Asn-$(Glu)_5$des $Pro^{36}$, $Pro^{37}$, $Pro^{38}$ [$Asp^{28}$] Exendin-4(1-39)-$NH_2$,
des $Pro^{36}$, $Pro^{37}$, $Pro^{38}$ [$Asp^{28}$] Exendin-4(1-39)-$(Lys)_6$-$NH_2$,
H-$(Lys)_6$-des $Pro^{36}$, $Pro^{37}$, $Pro^{38}$ [$Asp^{28}$] Exendin-4(1-39)-$(Lys)_6$-$NH_2$,
H-Asn-$(Glu)_5$-des $Pro^{36}$, $Pro^{37}$, $Pro^{38}$ [$Asp^{28}$] Exendin-4(1-39)-$(Lys)_6$-$NH_2$,
H-$(Lys)_6$-des $Pro^{36}$ [$Trp(O_2)^{25}$, $Asp^{28}$] Exendin-4(1-39)-$Lys_6$-$NH_2$,
H-des $Asp^{28}$ $Pro^{36}$, $Pro^{37}$, $Pro^{38}$ [$Trp(O_2)^{25}$] Exendin-4(1-39)-$NH_2$,
H-$(Lys)_6$-des $Pro^{36}$, $Pro^{37}$, $Pro^{38}$ [$Trp(O_2)^{25}$, $Asp^{28}$] Exendin-4(1-39)-$NH_2$,
H-Asn-$(Glu)_5$-des $Pro^{36}$, $Pro^{37}$, $Pro^{38}$ [$Trp(O_2)^{25}$, $Asp^{28}$] Exendin-4(1-39)-$NH_2$,
des $Pro^{36}$, $Pro^{37}$, $Pro^{38}$ [$Trp(O_2)^{25}$, $Asp^{28}$] Exendin-4(1-39)-$(Lys)_6$-$NH_2$,
H-$(Lys)_6$-des $Pro^{36}$, $Pro^{37}$, $Pro^{38}$ [$Trp(O_2)_{25}$, $Asp^{28}$] Exendin-4(1-39)-$(Lys)_6$-$NH_2$,
H-Asn-$(Glu)_5$-des $Pro^{36}$, $Pro^{37}$, $Pro^{38}$ [$Trp(O_2)^{25}$, $Asp^{28}$] Exendin-4(1-39)-$(Lys)_6$-$NH_2$,
H-$(Lys)_6$-des $Pro^{36}$ [$Met(O)^{14}$, $Asp^{28}$] Exendin-4(1-39)-$Lys_6$-$NH_2$,
des $Met(O)^{14}$ $Asp^{28}$ $Pro^{36}$, $Pro^{37}$, $Pro^{38}$ Exendin-4(1-39)-$NH_2$,
H-$(Lys)_6$-des$Pro^{36}$, $Pro^{37}$, $Pro^{38}$ [$Met(O)^{14}$, $Asp^{28}$] Exendin-4(1-39)-$NH_2$,
H-Asn-$(Glu)_5$-des $Pro^{36}$, $Pro^{37}$, $Pro^{38}$ [$Met(O)^{14}$, $Asp^{28}$] Exendin-4(1-39)-$NH_2$,
des $Pro^{36}$, $Pro^{37}$, $Pro^{38}$ [$Met(O)^{14}$, $Asp^{28}$] Exendin-4(1-39)-$(Lys)_6$-$NH_2$,
H-$(Lys)_6$-des $Pro^{36}$, $Pro^{37}$, $Pro^{38}$ [$Met(O)^{14}$, $Asp^{28}$] Exendin-4(1-39)-$(Lys)_6$-$NH_2$,
H-Asn-$(Glu)_5$ des $Pro^{36}$, $Pro^{37}$, $Pro^{38}$ [$Met(O)^{14}$, $Asp^{28}$] Exendin-4(1-39)-$(Lys)_6$-$NH_2$,
H-$Lys_6$-des $Pro^{36}$ [$Met(O)^{14}$, $Trp(O_2)^{25}$, $Asp^{28}$] Exendin-4(1-39)-$Lys_6$-$NH_2$,
H-des $Asp^{28}$ $Pro^{36}$, $Pro^{37}$, $Pro^{38}$ [$Met(O)^{14}$, $Trp(O_2)^{25}$] Exendin-4(1-39)-$NH_2$,
H-$(Lys)_6$-des $Pro^{36}$, $Pro^{37}$, $Pro^{38}$ [$Met(O)^{14}$, $Asp^{28}$] Exendin-4(1-39)-$NH_2$,
H-Asn-$(Glu)_5$-des $Pro^{36}$, $Pro^{37}$, $Pro^{38}$ [$Met(O)^{14}$, $Trp(O_2)^{25}$, $Asp^{28}$] Exendin-4(1-39)-$NH_2$,
des $Pro^{36}$, $Pro^{37}$, $Pro^{38}$ [$Met(O)^{14}$, $Trp(O_2)^{25}$, $Asp^{28}$] Exendin-4(1-39)-$(Lys)_6$-$NH_2$,
H-$(Lys)_6$-des $Pro^{36}$, $Pro^{37}$, $Pro^{38}$ [$Met(O)^{14}$, $Trp(O_2)^{25}$, $Asp^{28}$] Exendin-4(S1-39)-$(Lys)_6$-$NH_2$,
H-Asn-$(Glu)_5$-des $Pro^{36}$, $Pro^{37}$, $Pro^{38}$ [$Met(O)^{14}$, $Trp(O_2)^{25}$, $Asp^{28}$] Exendin-4(1-39)-$(Lys)_6$-$NH_2$;

or a pharmaceutically acceptable salt or solvate of any one of the afore-mentioned Exedin-4 derivative.

Hormones are preferably hypophysis hormones or hypothalamus hormones or regulatory active peptides or antagonists of said hormones, preferably as listed in Rote Liste, ed. 2008, Chapter 50. Examples of hormones are Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

Pharmaceutically acceptable salts are for example acid addition salts and basic salts. Acid addition salts are e.g. HCl or HBr salts. Basic salts are e.g. salts having a cation selected from alkali or alkaline, e.g. $Na^+$, or $K^+$, or $Ca^{2+}$, or an ammonium ion $N^+(R_1)(R_2)(R_3)(R_4)$, wherein $R_1$ to $R_4$ independently of each other mean: hydrogen, an optionally substituted $C_1$-$C_6$-alkyl group, an optionally substituted $C_2$-$C_6$-alkenyl group, an optionally substituted $C_6$-$C_{10}$-aryl group, or an optionally substituted $C_6$-$C_{10}$-heteroaryl group. Further examples of pharmaceutically acceptable salts are described in "Remington's Pharmaceutical Sciences" 17. Ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

All parts of the closure system can be manufactured by standard technologies such as rubber molding, injection molding for plastic parts, aluminum crimp cap manufacture, and injection needle manufacturing technologies. Clean parts manufacturing and sterilization technologies can be applied. Feeding the closures on the filling line can be done by standard technologies. The principles for closure techniques (e.g. crimping of aluminum caps) are common knowledge. The outer dimensions of the closure system and the interface between cartridge and device are similar to existing injection device systems. Adaptations can be easily made, either to the housing insert, closing means and/or to the cartridge to enable the system to be compatible with a variety of typical injection devices. In other words, the cartridge according to the present invention can be assembled with a syringe, an injection pen, an autoinjector device, or any other injection device where the injection is driven by external or internal forces (e.g. manual, electrical, mechanical, pneumatic, osmosis, etc.).

BRIEF DESCRIPTION OF THE FIGURES

Without any limitation, the instant invention will be explained in greater detail below in connection with preferred embodiments and with reference to the drawings in which:

FIG. 2B is a schematic view of a needle system designed for interaction with the cartridge of FIG. 2A, provided as separate item;

FIG. 2C is a schematic view of a tamper-proof plug designed for interaction with the cartridge of FIG. 2;

FIG. 2D is a schematic view of a tamper-proof cap designed for interaction with the cartridge of FIG. 2;

FIG. 3B shows the distal end of the cartridge of FIG. 3A after closing and crimping;

FIG. 5F is a sectional view of the distal end of the cartridge of FIG. 5C after withdrawal of contents;

FIG. 6C is a sectional view of the distal end of the cartridge of FIG. 6A with an attached needle system in venting position;

FIG. 7B is a sectional view of the distal end of the cartridge of FIG. 7A with an attached needle system.

DETAILED DESCRIPTION

Figure 1:
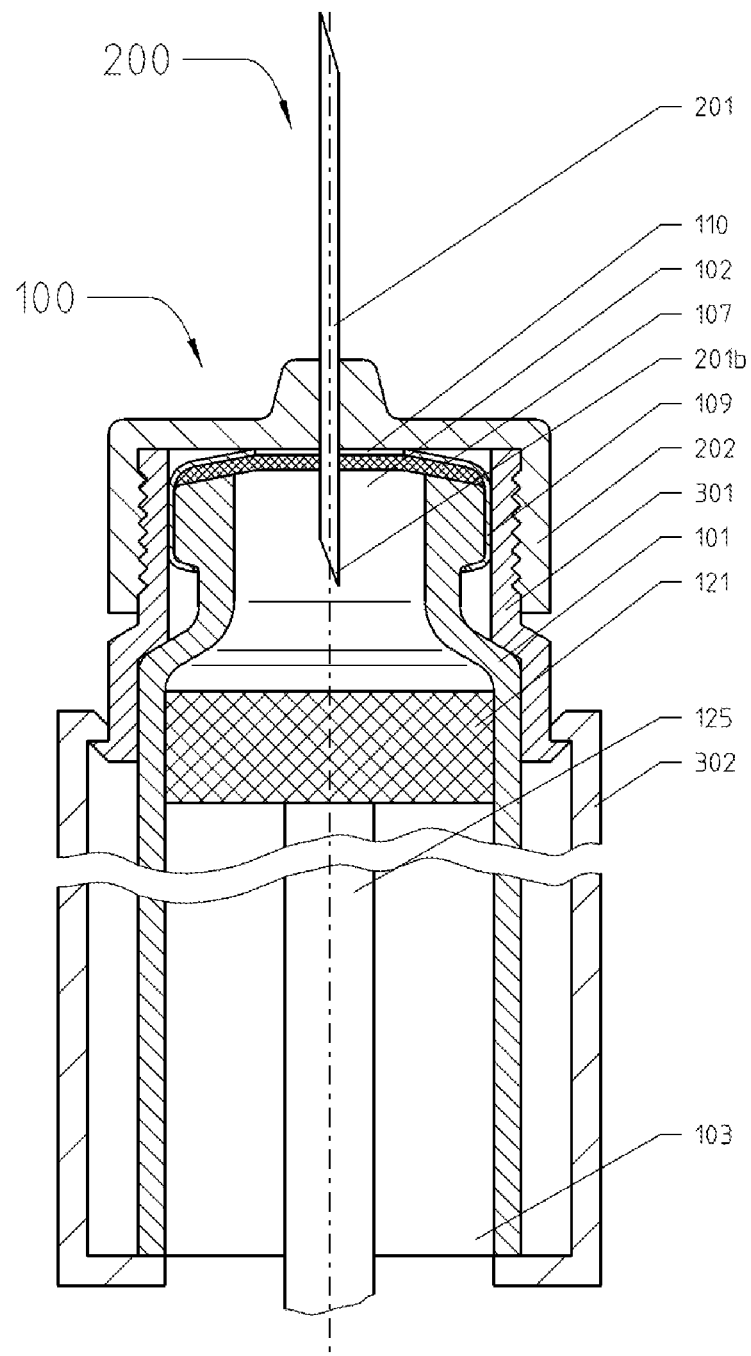
FIG. 1 is a schematic view of an assembled single compartment cartridge with an activated needle according to the prior art.

Referring to FIG. 1, there is illustrated an exemplary assembled closure system according to prior art. The closure system, generally referenced with the number 100, includes a cartridge barrel 101 which has a distal open end 102 and a proximal open end 103, opposite to the open end 102. The proximal open end 103 is closed by a piston 121 which is attached to or in direct contact with a plunger 125. The distal open end 102 is closed by a rubber sealing disc 107 which is fixed to the cartridge barrel 101 by crimping of an aluminum cap 109. The aluminum cap 109 has a central opening 110 that, by piercing the rubber sealing disc 107 with a needle, allows access to the contents of the cartridge.

FIG. 1 further shows a cartridge holder 302 of the assembled device that contains the cartridge barrel 101. The cartridge barrel 101 is retained within the cartridge holder 302 by means of a cartridge retainer 301. Alternatively the features of the cartridge retainer 301 may be combined with the cartridge holder 302. A needle system 200 features a needle hub 202. The needle hub 202 attaches to the screw thread of the cartridge retainer 301, thereby the needle 201 penetrates the rubber sealing disc 107 and the proximal needle tip 201b ends in the dead space area of the cartridge neck.

The closing process of such cartridges encompasses attachment of aluminum caps 109 with inserted rubber sealing discs 107 to the cartridge barrel 101 and fixation by a crimping step. The needle system 200 is attached to the cartridge such that the needle 201 essentially lies in the longitudinal axis (shown in dashed lines) of the barrel 101.

Figure 2A:
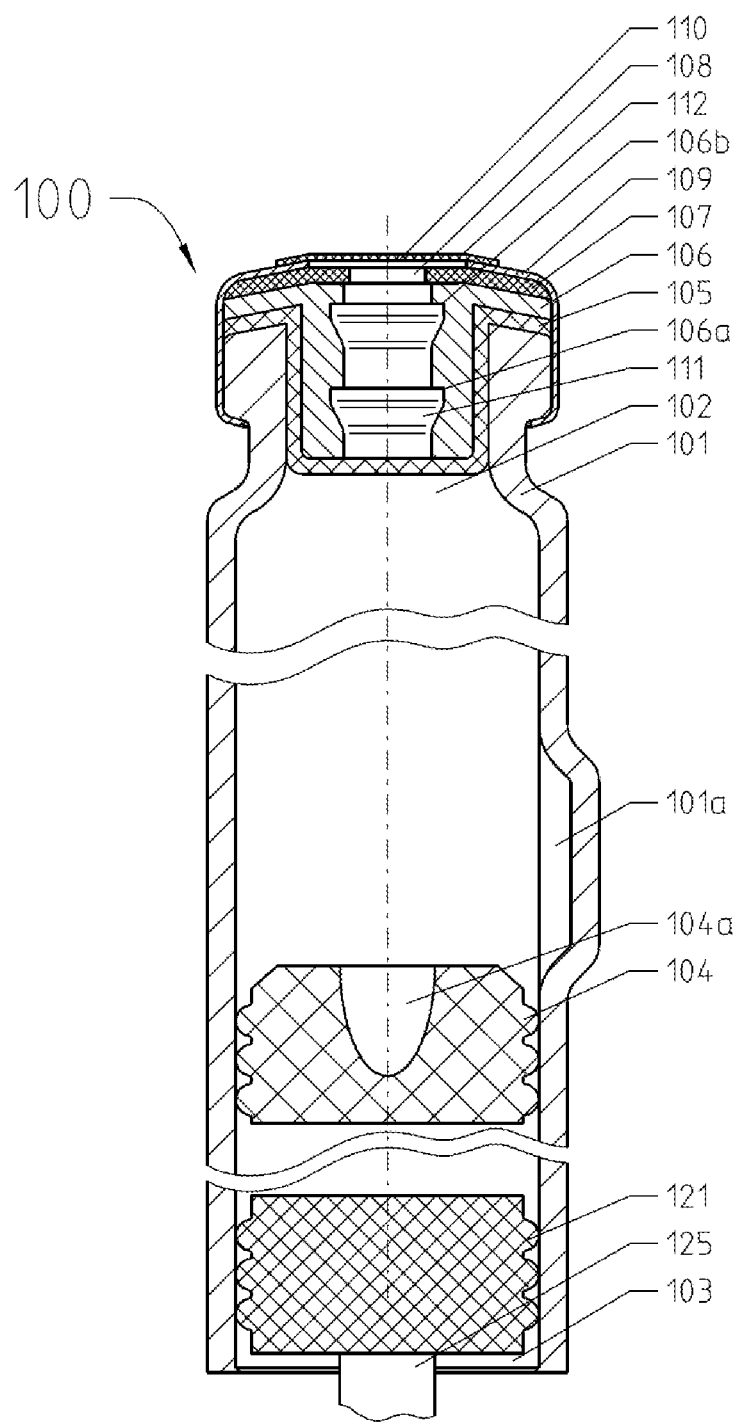
FIG. 2A is a schematic view of an assembled cartridge according to a first embodiment of the present invention.

Referring to FIG. 2A, there is illustrated an exemplary assembled closure system for a cartridge according to the invention. The closure system, generally referenced with the number 100, includes a cartridge barrel 101 which has a distal open end 102 and a proximal open end 103, opposite to the open end 102. The proximal open end 103 is closed by a conical piston 104 and a second piston 121. The distal open end 102 is closed by a rubber stopper 105, into which a housing insert 106 is placed. On top of the housing insert a rubber sealing disc 107 with a central opening 108 may optionally be placed. All closure parts, rubber stopper 105, housing insert 106, and rubber sealing disc 107 are fixed to the cartridge barrel 101 by crimping of an aluminum cap 109. The aluminum cap 109 has a central opening 110 that allows access to the inner void space 111 of the housing insert 106. A film seal 112 is attached onto the aluminum cap 109 to cover the central openings 108 and 110 and to seal the inner void space 111 against the environment. In the absence of optional rubber sealing disc 107 a seal is made between the outside edge of rubber stopper 105 and the aluminum cap 109 which, in cooperation with film seal 112, protects the inner void space 111 against the environment.

As a first step in the closing process of cartridge barrel 101, the rubber stopper 105 is inserted into the distal open end 102, thereby sealing the cartridge barrel 101. Secondly, the housing insert 106 is set into the void inner space of the rubber stopper 105. The aluminum cap 109 with attached film seal 112 and inserted rubber sealing disc 107 is then placed over the top of the cartridge assembly and by a crimping step the closure system is fixed to the cartridge barrel 101.

The assembly of the individual parts of the closure system does not need to be completely performed during the manufacturing process of the product. The closure system can also be provided partially pre-assembled. Pre-assembly of the aluminum closure cap encompasses the insertion of the optional rubber sealing disc 107 into the aluminum crimp cap 109 and attaching the film seal 112. Pre-assembly of the closure insert assembly encompasses the insertion of the housing insert 106 into the rubber stopper 105.

For all examples described herein, all steps of pre-assembling the closure system parts are performed under conditions that guarantee low-particulate matter status of the assemblies, where necessary. Further, for applications where sterile and non-pyrogene packaging systems are required, adequate treatment (e.g. washing and sterilization processes) is applied to the individual components prior to assembly.

To allow injection, a needle system, generally referenced with the number 200, is to be inserted into the inner void space 111 of the housing insert 106. Referring to FIG. 2B, the needle system 200 includes a needle 201 with a distal needle tip 201a and a proximal needle tip 201b, a preferably overmolded needle hub 202, an inner needle cap 203, and an outer needle cover 204 and a needle housing closure 205. The inner needle cap 203 may be combined with or adhered to the outer needle cover 204 or may optionally be omitted.

To minimize pain of injection and prevent damage to the needle it is important that the needle 201 is attached as straight as possible relative to the longitudinal axis of the injection device. The needle hub 202 is designed to engage features of the inner void space 111 of the housing insert 106 of the closure system. The diameter, length and features of both the needle hub 202 and the inner void space 111 are designed to position the needle 201 as close to the longitudinal axis of closure system 100 as possible.

Furthermore, the needle hub 202 and housing insert 106 have features to control the axial position of the proximal needle tip 201b relative to the proximal face of the housing insert 106. The example shown in FIGS. 2A and 2B features a two-step insertion process, achieved by having two sets of mating features, a proximal mating feature 106a and a distal mating feature 106b, on the internal wall of housing insert 106. In a first needle insertion position the mating features 202a of the needle hub 202 engage the distal mating feature 106b of the housing insert 106. In this position the proximal needle tip 201b does not protrude beyond the proximal face of the housing insert 106. In a second needle insertion position the mating features 202a of the needle hub 202 engage the proximal mating feature 106a of the housing insert 106. In this position the proximal needle tip 201b protrudes beyond the proximal face of the housing insert 106 by an amount designed to guarantee that the proximal needle tip 201b always pierces the rubber stopper 105. Thus the mating features of the needle hub and the corresponding mating features of the housing insert are designed as attachment means and retaining means for guiding and retaining the needle system 200 in the housing insert 106.

An embodiment with a one-step needle insertion is also possible (not shown). In this embodiment the distal mating feature 106b on the internal wall of the housing insert 106 would not be present.

By appropriate design of the mating features of both needle hub 202 and housing insert 106 it is possible to bias the needle such that its axial position is controlled by a single datum surface on each of the needle hub 202 and housing insert 106. This can be achieved having nominal interference between angled contact surfaces of the mating features which drives the datum surfaces of the mating features into contact. Controlling axial needle position in this manner will minimize the effect of any manufacturing tolerances on the position of the proximal needle tip 201b relative to the proximal face of the housing insert 106.

The mating features are further designed to ensure that once attached the needle cannot be removed, either manually or by internal forces during the injection process. To achieve this, the mating features of the needle hub 202 and housing insert 106 are designed such that they will be a snap-fit during needle attachment. The example shown, with non-removable needle, would be suitable for a single-use injection device. A further embodiment is also possible where the mating features are designed to permit the removal of an inserted needle. This may be necessary if multiple injections are to be delivered from the same cartridge. In this embodiment the snap-fit would be designed to be sufficiently strong to retain the needle during the injection, but weak enough to permit manual removal.

Prior to insertion of the needle, the film seal 112 is removed to open the inner void space 111. The needle housing closure 205 is removed from the needle system 200. Then, the injection needle is inserted to a first position without piercing the rubber stopper 105, but being no longer removable due to the snap-fit of the mating features of the needle hub 202 interacting with the distal mating features 106b of the housing insert 106. By further pushing the needle system 200 into the housing insert 106 the mating features of the needle hub 202 engage with the proximal mating features 106a of the housing insert 106. The proximal needle tip 201b penetrates the rubber stopper 105 and the needle is locked into the second position. When the needle housing 204 is then removed, the distal needle tip 201a is still protected by the inner needle cap 203. Shortly before injection, the inner needle cap 203 is removed and the injection system is ready for injection.

Alternatively, the film seal 112 can be sterilized by wiping with an alcohol swab prior to needle attachment. The needle system 200 can then be attached without the need to remove the film seal 112. During needle attachment the proximal needle tip 201b pierces the film seal 112 and allows the needle hub 202 to be inserted into the inner void space 111 of housing insert 106. If this alternative needle attachment method were followed a simpler embodiment of the closure could be used. The film seal 112 can be positioned directly on the housing insert 105, underneath the aluminum cap 109, sealing the inner void space 111. This simpler embodiment would remove the need for an additional seal to protect the inner void space 111 either the seal between the sealing disc 107 and the aluminum cap 109 or the alternative seal between the outside edge of rubber stopper 105 and the aluminum cap 109.

FIGS. 2C and 2D show further alternatives to the film seal 112 to protect the inner void space 111 of the housing insert 106 against contamination. FIG. 2C shows an exemplary tamper-proof plug 126 which is to be removed prior to needle attachment. FIG. 2D shows a tamper-proof cap 127, covering the inner void space 111 of the housing insert 106 and being pulled off prior to needle insertion.

An advantage of the proposed two-step needle attachment process is that the rubber stopper is not pierced during the first step of the attachment. Therefore, any powder content of the cartridge cannot fall into the needle and cause it to become blocked. Once mixing of the powder content with diluent has been completed the needle can now be advanced to its second position where the rubber stopper 105 is penetrated.

The second step of the needle attachment can be performed manually, however, it is advantageous if this second step is performed automatically immediately prior to injection. This automatic needle advancement from the first insertion position to the second insertion position can be achieved in a number of ways. For example, the user could press the device against the skin whereupon the skin presses on a flange of the needle hub 202. However, the forces required to advance the needle may cause discomfort. Therefore, it is preferable if the automatic needle advancement is achieved as part of the action of triggering the injection itself. For example, features of the device might interact with a flange on the needle hub 202. When the injection is triggered the cartridge could advance under the action of the injection spring (or alternative energy source) towards the needle, which could be designed to be restrained relative to the body of the device, thus causing the needle to advance to the second position. An embodiment with a one-step needle attachment is also possible. In this embodiment the needle is inserted directly into a position where the proximal needle tip 201b penetrates the rubber stopper 105.

Referring to FIG. 3A to 3E, there is illustrated an exemplary assembled closure system of a cartridge according to the invention. Where applicable, identical parts are numbered with the same figures as dedicated in example 1.

In addition to example 1, the preferred embodiment of example 2 has attached a pre-assembled needle system 200 to the closure system 100. Thus, a film seal 112 is not required as the inner void space 111 is protected against contamination by the inserted needle system 200 and a seal made by an interference fit between the rubber sealing disc 107 and the preferably overmolded needle hub 202. Alternatively the rubber sealing disc 107 may be omitted and the inner void space 111 is protected by a seal made by an interference fit between the preferably overmolded needle hub 202 and the housing insert 106. Two pistons, 104 and 121, are inserted into the dual chamber cartridge system.

Figure 3A:
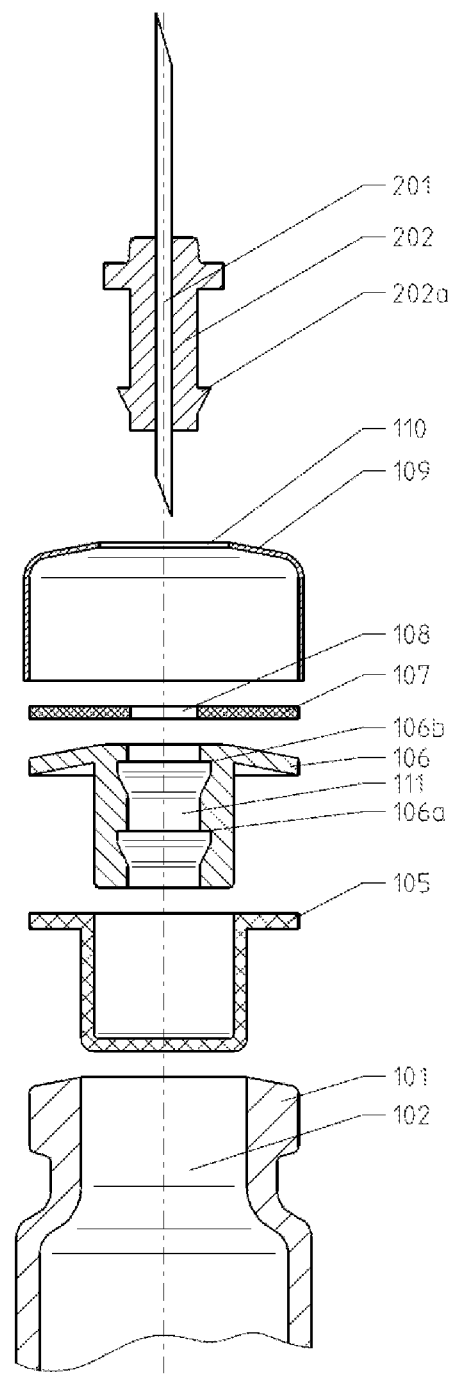
FIG. 3A is an exploded view of the distal end of a combination of a cartridge similar to the cartridge of FIG. 2A and an integrated needle system.
Figure 3C:
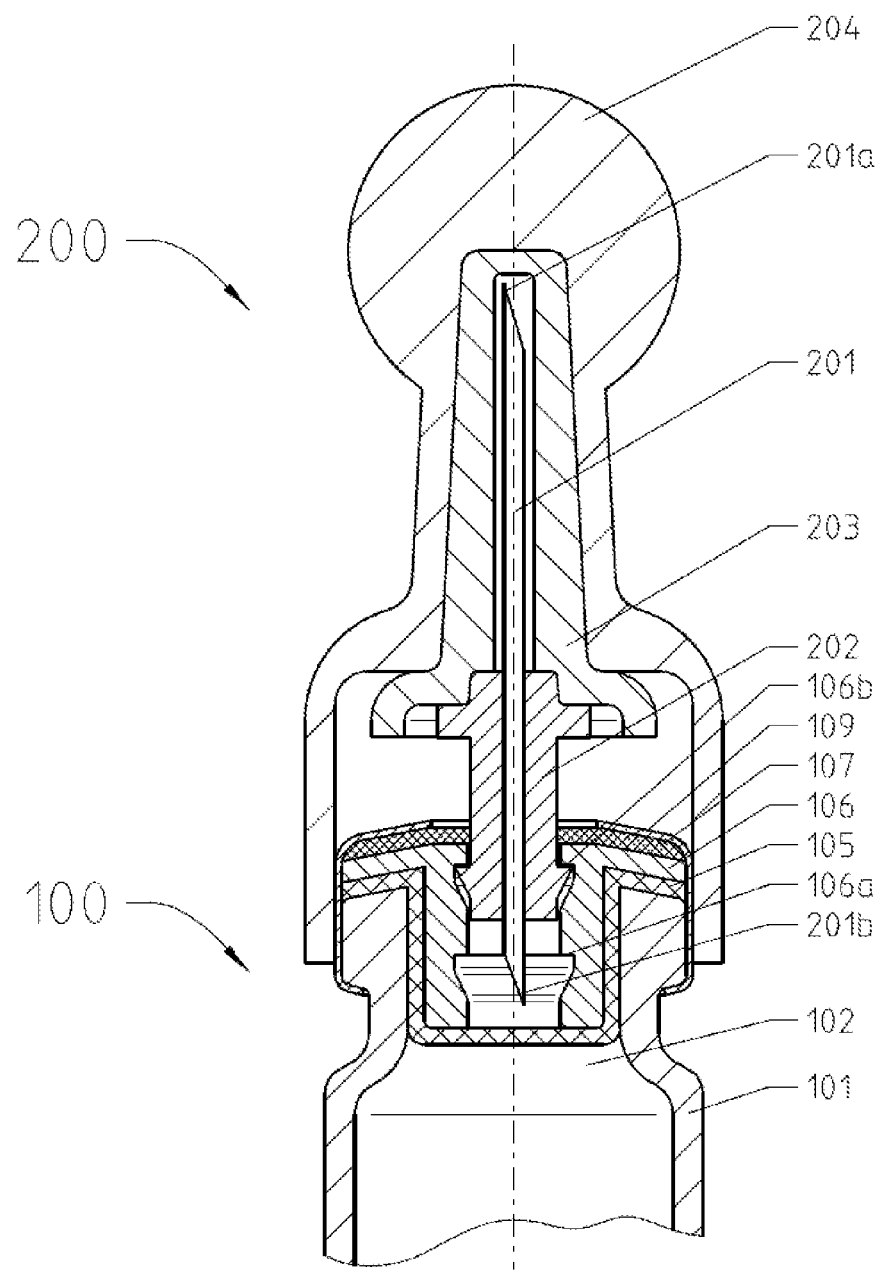
FIG. 3C shows the distal end of the cartridge of FIG. 3A after attaching the integrated needle system, prior to needle activation.

Closing of the cartridge system is performed in the same way as described in example 1 (FIG. 3B). As a further step, the pre-assembled needle system 200 is attached to the closure system and positioned in the first inactive position, where the rubber stopper 105 is not pierced by the proximal needle tip 201b (FIG. 3C). The injection needle is covered by an inner needle cap 203 and a needle housing 204. In this example the inner needle cap 203 would be manufactured in a rubber material, and would seal against the needle hub 202, in order to maintain the sterility of the needle.

The assembly of the individual parts of the closure system does not need to be completely performed during the manufacturing process of the product. The closure system can also be provided partially pre-assembled. Pre-assembly may be performed as described above with respect to example 1.

Pre-assembly of the needle system 200 encompasses the attachment of the inner needle cap 203 and an outer needle cover 204, if required. To facilitate handling and automated manufacturing processes, manifold pre-assembled needle systems can be placed into nests.

Figure 3D:
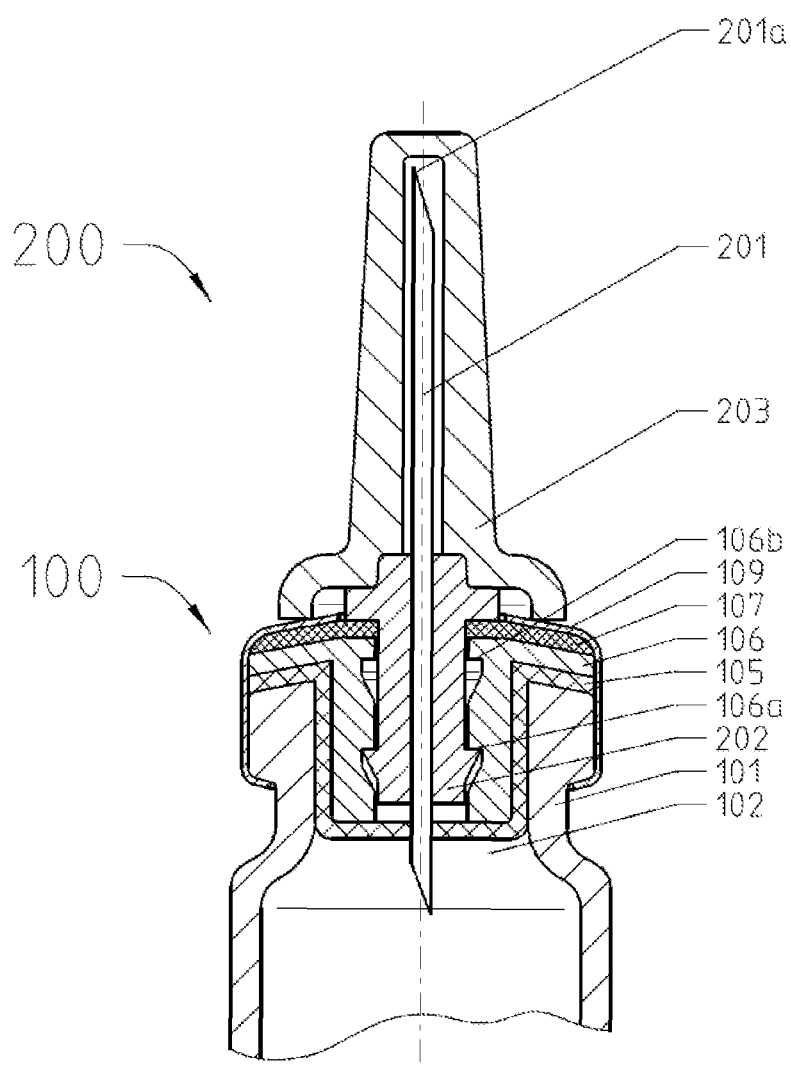
FIG. 3D shows the distal end of the cartridge of FIG. 3A after attaching the integrated needle system, locked in activated needle position.

To allow injection, the system is activated by further pushing the needle system 200 into the housing insert 106. The mating features 202a of the needle hub 202 disengage from the distal mating features 106b of the housing insert 106 and engage with the proximal mating features 106a. FIG. 3D shows the cartridge system locked in the activated needle position. Upon activation, the proximal needle tip 201b penetrates the rubber stopper 105 and the needle is locked into position such that it cannot return to the first, inactive, insertion position. Then, the needle housing 204 is removed, leaving the distal needle tip 201a protected by the inner needle cap 203. Shortly before injection, the inner needle cap 203 is removed and the injection system is ready for injection. The inner needle cap 203 may alternatively be combined with or adhered to the outer needle cover 204 and therefore both outer needle cover 204 and inner needle cover 203 are removed in a single user action.

An advantage of the proposed integrated needle is that the number of handling steps for the user is reduced, making the overall device system easier and more convenient to use. Furthermore, the risk of causing damage to the needle, such as blockage or bending of the needle, or damage to the cartridge seal during manual attachment of a separate needle is eliminated.

A number of syringe or cartridge designs exist where the needle is incorporated into the glass body of the cartridge, either as a pre-attached needle assembly or where the needle is glued-in (staked) to the syringe body. Although these syringes also have the advantage of not attaching a separate needle they also have a significant disadvantage if powder is present in the body of the syringe or cartridge. During storage or transit powder may enter the needle itself and may cause the needle to become blocked. The proposed integrated needle does not pierce the rubber stopper in its assembled condition. Therefore, any powder content of the cartridge cannot fall into the needle and cause it to become blocked. Once mixing of the powder content with diluent has been completed the needle can now be advanced to its activated position where the rubber stopper 105 is penetrated.

The activation step of the needle attachment can be performed manually, by pressing the inner needle cap 203 towards the housing insert 106 prior to removal of the inner needle cap 203. However, it is advantageous if this activation step is performed automatically immediately prior to injection. This automatic needle advancement from the first insertion position to the second insertion position can be achieved in a number of ways as described with respect to example 1.

Figure 3E:
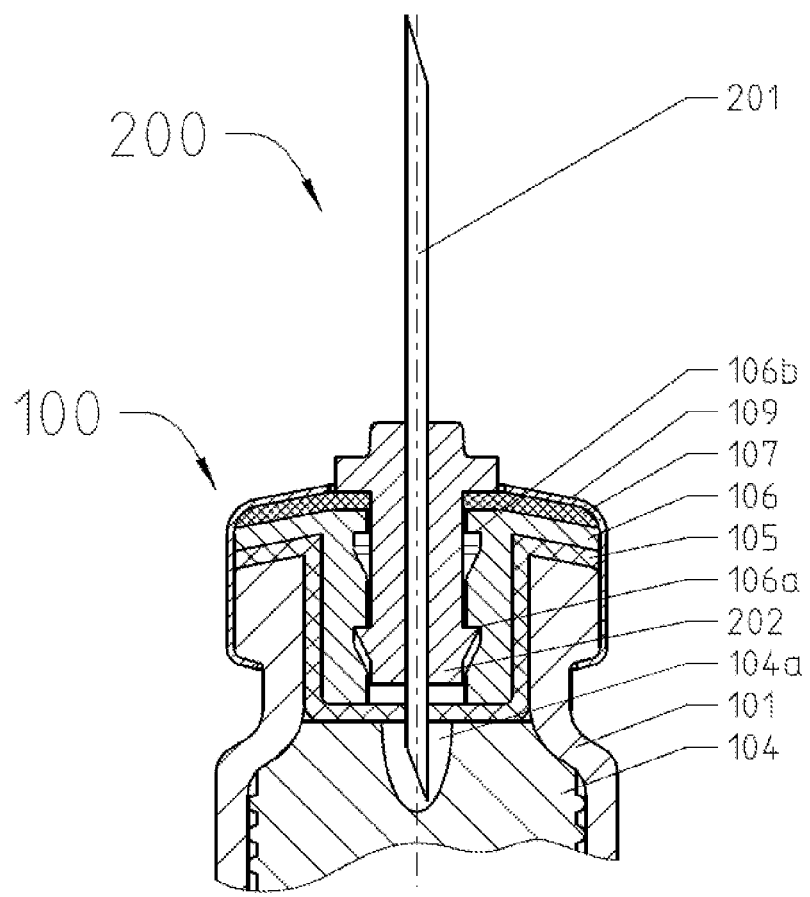
FIG. 3E shows the distal end of the cartridge of FIG. 3A after withdrawal of the contents.

FIG. 3E shows the cartridge system after withdrawal of the contents. The conical piston 104 has an in-molded needle cavity 104a and is shaped such that at contact of the piston 104 with the rubber stopper 105 at fully activated needle position the dead space in between is reduced to the volume of the needle cavity 104a.

Figure 4:
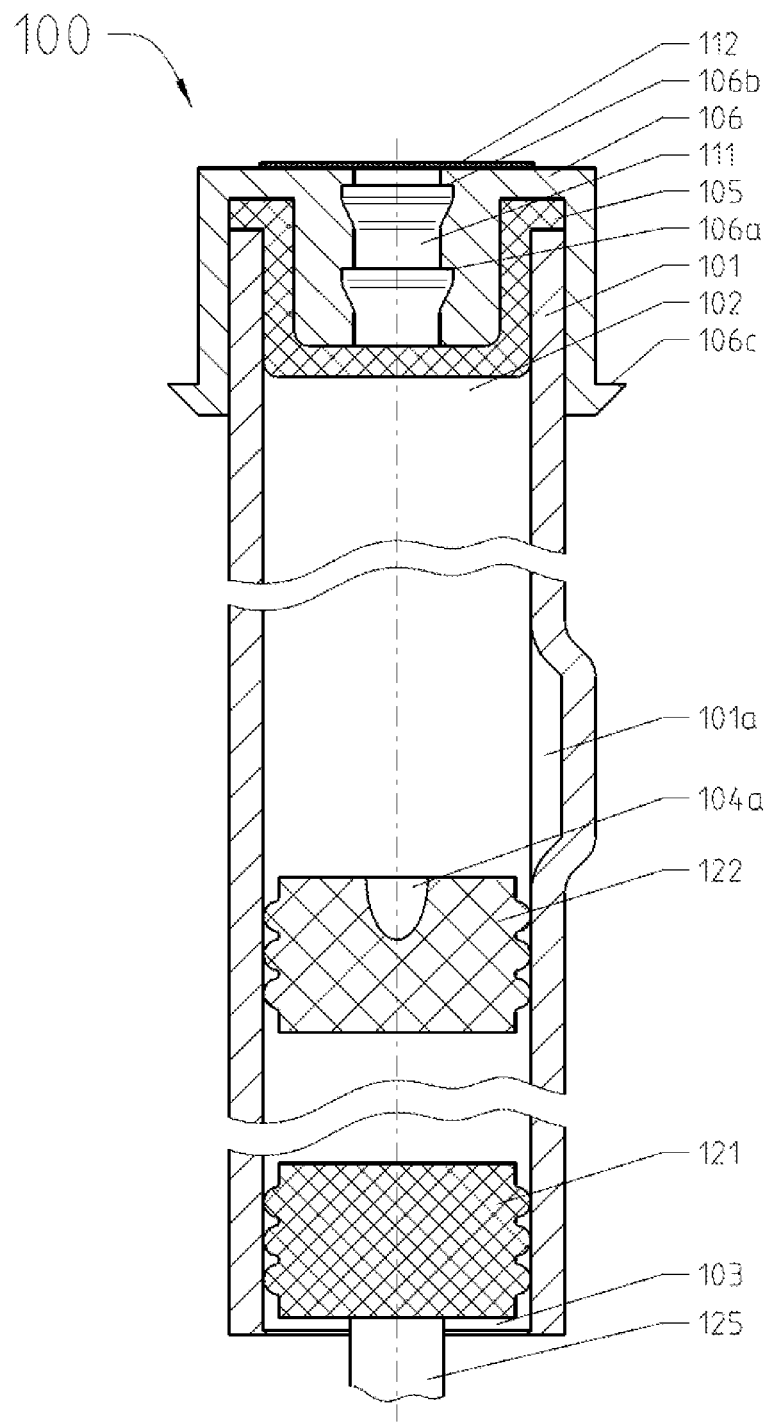
FIG. 4 is a schematic view of an assembled cartridge according to a second embodiment of the present invention.

Referring to FIG. 4, there is illustrated an exemplary assembled closure system incorporating a snap-fit to the injection device according to the invention. The closure system, generally referenced with the number 100, includes a cartridge barrel 101 which has a distal open end 102 and a proximal open end 103, opposite to the open end 102. The proximal open end 103 is closed adjacent to the bypass 101a by a cylindrical piston 122 with in-molded needle cavity 104a, and with an end piston 121, thereby forming a dual chamber cartridge. The distal open end 102 is closed by a rubber stopper 105, into which a housing insert 106 is placed. The housing insert 106 bears two snaps 106c that overlap along the side of the cartridge and act as retainer once the cartridge is mounted into an injection device assembly (not shown). A film seal 112 is attached onto the housing insert 106 to cover and to seal the inner void space 111 against the environment.

As a first step in the closing process of cartridges, the rubber stopper 105 is inserted into the distal open end 102, thereby sealing the cartridge barrel 101. Secondly, the housing insert 106 is set into the void inner space of the rubber stopper 105. The fit of the housing insert 106 into the rubber stopper 105 and cartridge barrel 101 is designed such that the side walls of the rubber stopper are compressed between the cartridge barrel 101 and the housing insert 106. This compression seals the end of the cartridge barrel 101 and also ensures that the housing insert is retained by friction. A so closed cartridge may be transferred to the assembly with an injection device.

The assembly of the individual parts of the closure system does not need to be completely performed during the manufacturing process of the product, the closure system can also be provided partially pre-assembled. Pre-assembly of the closure insert assembly encompasses the insertion of the housing insert 106 into the rubber stopper 105.

In examples 1 and 2 it is assumed that the assembled and closed cartridge is further assembled into an injection device, for example an autoinjector. Typically it is expected that this will require the addition of a retaining component that will fix the cartridge into the device. In example 3 (and subsequent example 4) snap-fit cartridge retaining features 106c are incorporated into the housing insert 106.

The snap-fit retaining features 106c have two functions. Firstly, they secure the cartridge into the device without the need for an additional restraining component. Secondly, they secure the housing insert 106 relative to the end of the cartridge barrel 101 and prevent the cartridge closure 100 becoming detached from the cartridge barrel 101. This would be a particular concern in storage or transit where changes in air pressure and or temperature may cause expansion of the gases or liquids inside the cartridge which may overcome the friction between cartridge barrel 101, rubber stopper 105 and housing insert 106.

To allow injection, a needle system 200 as described in example 1 is attached to the closure system 100. Prior to insertion of the needle, the film seal 112 is removed to open the inner void space 111. The needle housing closure 205 is removed from the needle system 200. Then, the injection needle is inserted to a first position without piercing the rubber stopper 105, but being no longer removable due to the snap-fit of the mating features of the needle hub 202 interacting with the distal mating features 106b of the housing insert 106. By further pushing the needle system 200 into the housing insert 106 the mating features of the needle hub 202 engage with the proximal mating features 106a of the housing insert 106. The proximal needle tip 201b penetrates the rubber stopper 105 and the needle is locked into the second position. When the needle housing 204 is then removed, the distal needle tip 201a is still protected by the inner needle cap 203. Shortly before injection, the inner needle cap 203 is removed and the injection system is ready for injection.

Alternatively, the film seal 112 can be sterilized by wiping with an alcohol swab prior to needle attachment. The needle system 200 can then be attached without the need to remove the film seal 112. During needle attachment the proximal needle tip 201b pierces the film seal 112 and allows the needle hub 202 to be inserted into the inner void space 111 of housing insert 106.

The advantages for the two-step needle attachment are the same as those described for the two-step attachment of the needle in example 1. An embodiment with a one-step needle attachment is also possible. In this embodiment the needle is inserted directly into the position where the proximal needle tip 201b penetrates the rubber stopper 105.

Referring to FIG. 5A to 5F, there is illustrated a combination of a cartridge with snap-fit and a pre-assembled needle according to the invention. Where applicable, identical parts are numbered with the same figures as dedicated in examples before.

In addition to example 3, example 4 has a pre-assembled needle system 200 attached to the closure system 100. Therefore, a film seal 112 is not required as the inner void space 111 is protected against contamination by the addition of a sealing component, O-ring 206, between the inserted needle system 200 and the housing insert 106.

Figure 5A:
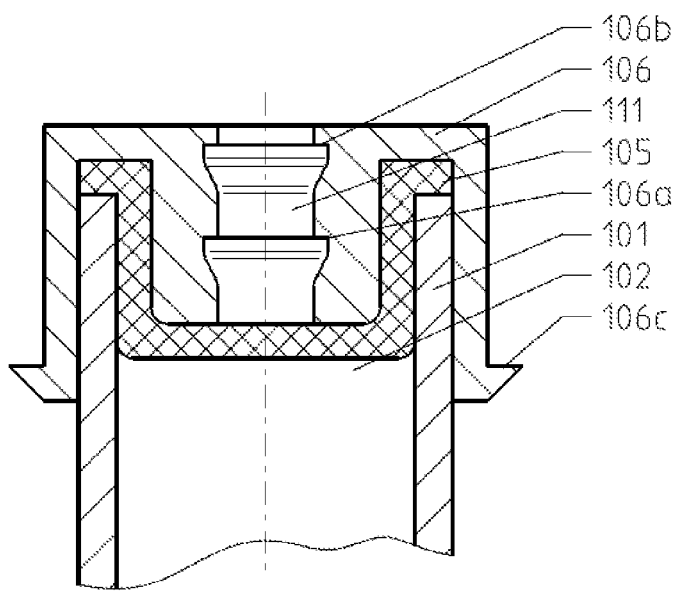
FIG. 5A is a sectional view of the distal end of the cartridge of FIG. 4.
Figure 5B:
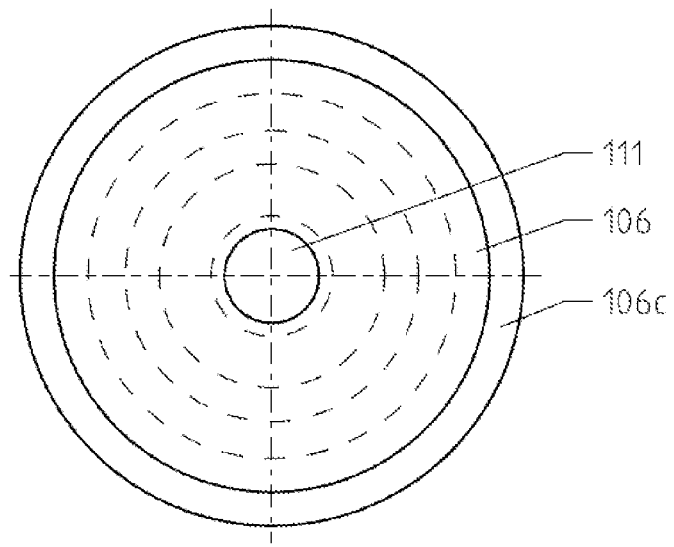
FIG. 5B is a top view of the distal end of the cartridge of FIG. 5A wherein the sleeve-like section is a 360 degree surrounding sleeve.
Figure 5C:
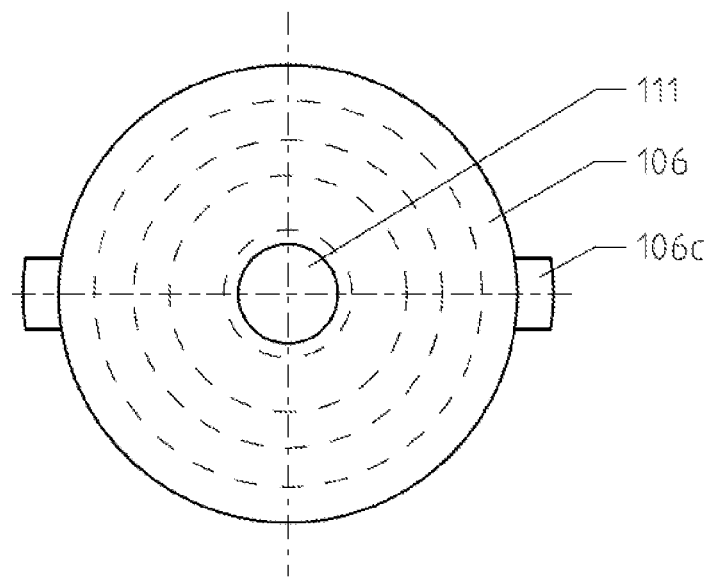
FIG. 5C is a top view of the distal end of the cartridge of FIG. 5A wherein the sleeve-like section is a 360 degree surrounding sleeve comprising 2 intersections and consists of 2 hooked arms.
Figure 5D:
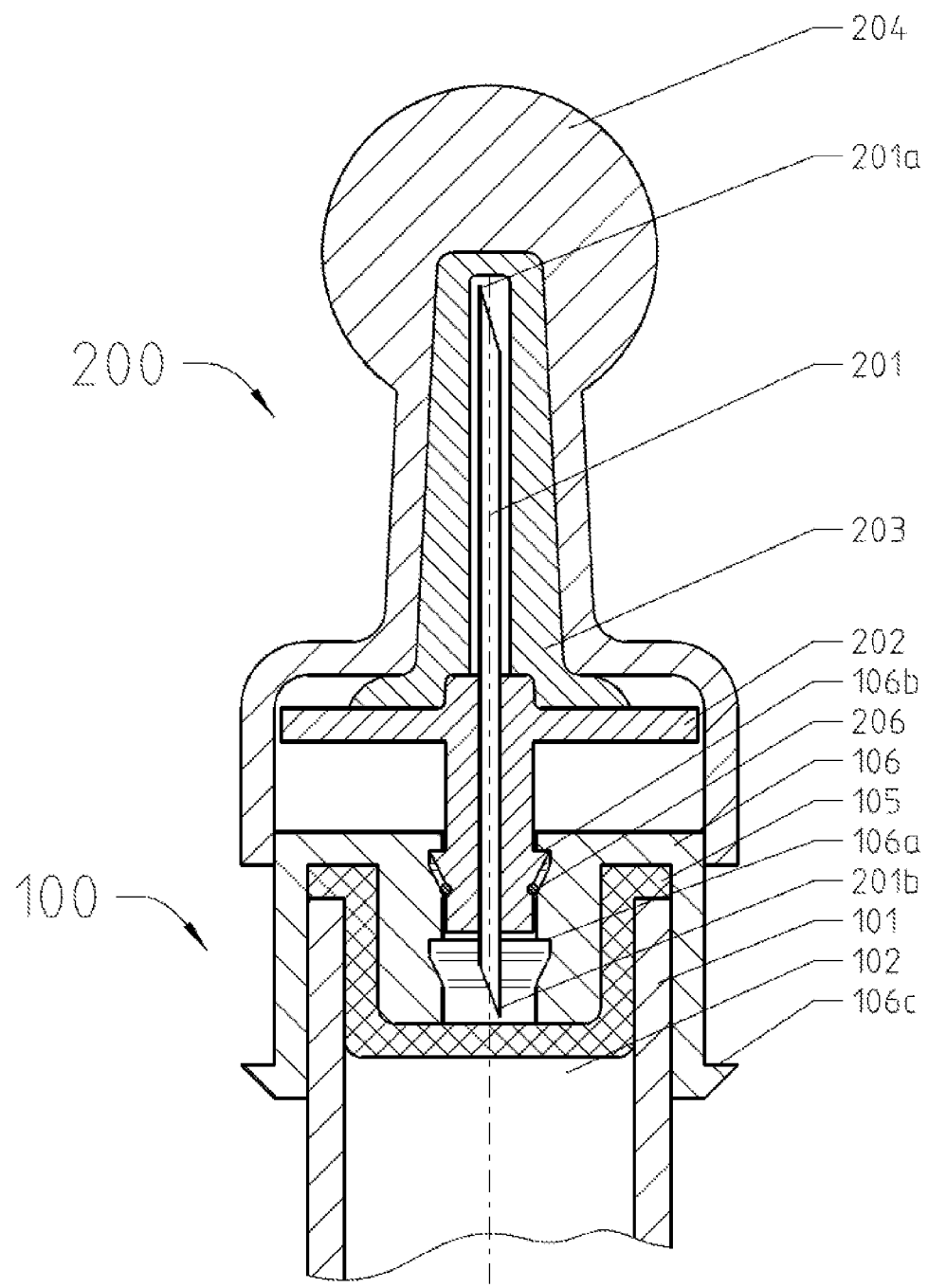
FIG. 5D is a sectional view of the distal end of the cartridge of FIG. 4 with an attached needle system.

Closing of the cartridge system is performed in the same way as described in example 3 (FIG. 5A). Alternative options for the housing insert 106 carrying the snap-fit cartridge retaining features 106c are shown in FIGS. 5B and 5C. As a further step, the pre-assembled needle system 200 is attached to the closure system and positioned in the first inactive position, where the rubber stopper 105 is not pierced by the proximal needle tip 201b (FIG. 5D). The injection needle is covered by an inner needle cap 203 and a needle housing 204.

Figure 5E:
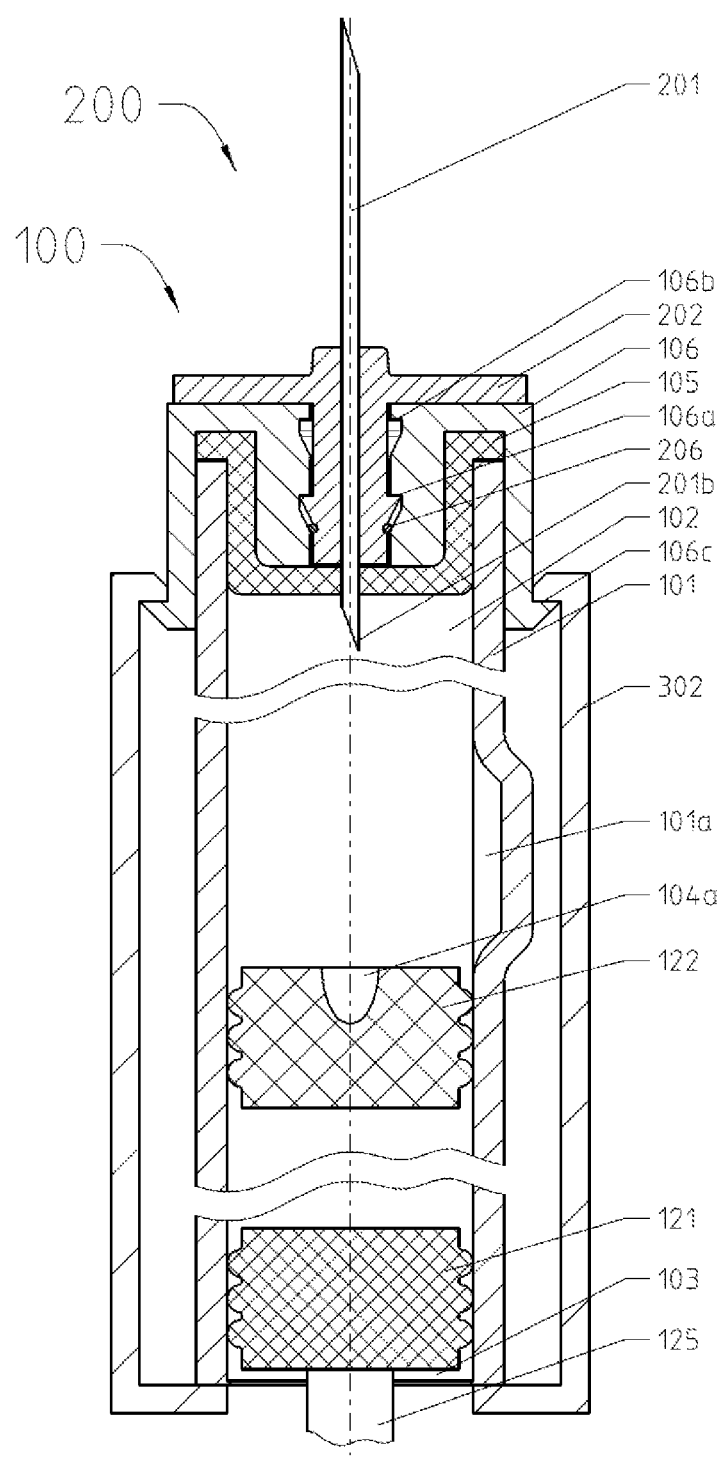
FIG. 5E is a schematic view of the cartridge of FIG. 4 with an activated needle.

In this example the inner needle cap 203 would be manufactured in a rubber material, and would seal against the needle hub 202, in order to maintain the sterility of the needle. The so closed cartridges with attached needle system 200 are transferred to the assembly with the injection device. FIG. 5E shows exemplary the cartridge system inserted into an injection device where the axial snap-fit 106c locks into a cartridge holder component 302.

If the assembly of the individual parts of the closure system is not completely performed during the manufacturing process of the product, the closure system can also be provided partially pre-assembled. Pre-assembly may be performed as described above with respect to examples 1 to 3.

Example 4 has similar snap-fit features 106c on the housing insert 106 as per example 3. In this respect example 4 has the same advantages as example 3.

To allow injection, an integrated needle system 200 as described in example 2, but with an additional needle O-ring 206 is to be used. The needle O-ring 206 has its seat below the mating feature on the needle hub 202 and seals the needle hub 202 against the housing insert 106, thereby protecting the inner void space 111 against contamination. Alternatively the O-ring 206 may be omitted and the inner void space 111 is protected by a seal made by an interference fit between the preferably overmolded needle hub 202 and the housing insert 106.

To allow injection, the system is activated by further pushing the needle system 200 into the housing insert 106. Thereby, the proximal needle tip 201b penetrates the rubber stopper 105 and the needle is locked into a second activated position where it cannot be removed from the housing insert 106. Then, the needle housing 204 is removed, still leaving the distal needle tip 201a protected by the inner needle cap 203. Shortly before injection, the inner needle cap 203 is removed and the injection system is ready for injection. The inner needle cap 203 may alternatively be combined with or adhered to the outer needle cover 204 and therefore both outer needle cover 204 and inner needle cover 203 are removed in a single user action.

FIG. 5F shows the cartridge system after withdrawal of the contents. The cylindrical piston 122 has an in-molded needle cavity 104a and is shaped such that at contact of the piston 122 with the rubber stopper 105 at fully activated needle position the dead space in between is reduced to the volume of the needle cavity 104a.

An advantage of the proposed integrated needle is that the number of handling steps for the user is reduced, making the overall device system easier and more convenient to use. Furthermore, the risk of causing damage to the needle, such as blockage or bending of the needle, or to the cartridge seal during manual attachment of a separate needle is eliminated.

The integrated needle of example 4 shares the same advantages as example 2 with respect to keeping powder away from the pre-attached needle and preventing possible needle blockage. Furthermore the integrated needle of example 4 is activated in the same manner as the integrated needle of example 2. Therefore, the same potential exists for automation of needle activation by the device mechanism.

Referring to FIG. 6A to 6E, there is illustrated an exemplary assembled vented closure system of a cartridge according to the invention. The closure system, generally referenced with the number 100, includes a cartridge barrel 101 which has a distal open end 102 and a proximal open end 103, opposite to the open end 102. Two pistons, a conical piston 104 with an in-molded needle cavity 104a, and a plunger stopper 121 with in-molded thread are inserted into the dual chamber cartridge system. The distal open end 102 is closed by a vented housing insert 115, tightened against the cartridge barrel 101 by a gasket 116 and containing a semi-permeable membrane 117. On top of the vented housing insert 115 a rubber sealing disc 107 with a central opening 108 is placed. All closure parts, the vented housing insert 115, the gasket 116, and the rubber sealing disc 107 are fixed to the cartridge barrel 101 by crimping of an aluminum cap 109. The aluminum cap 109 has a central opening 110 that allows access to the inner void space 111 of the housing insert 106. The preferred embodiment of example 5 has attached a pre-assembled needle system 200 to the closure system 100. A film seal 112, see example 1, is not required as the inner void space 111 is protected against contamination by the inserted needle system 200 and a seal made by an interference fit between the rubber sealing disc 107 and the needle hub 202. Alternatively the rubber sealing disc 107 may be omitted and the inner void space 111 is protected by a seal made by an interference fit between the inserted needle system 200 and the housing insert 106.

Figure 6A:
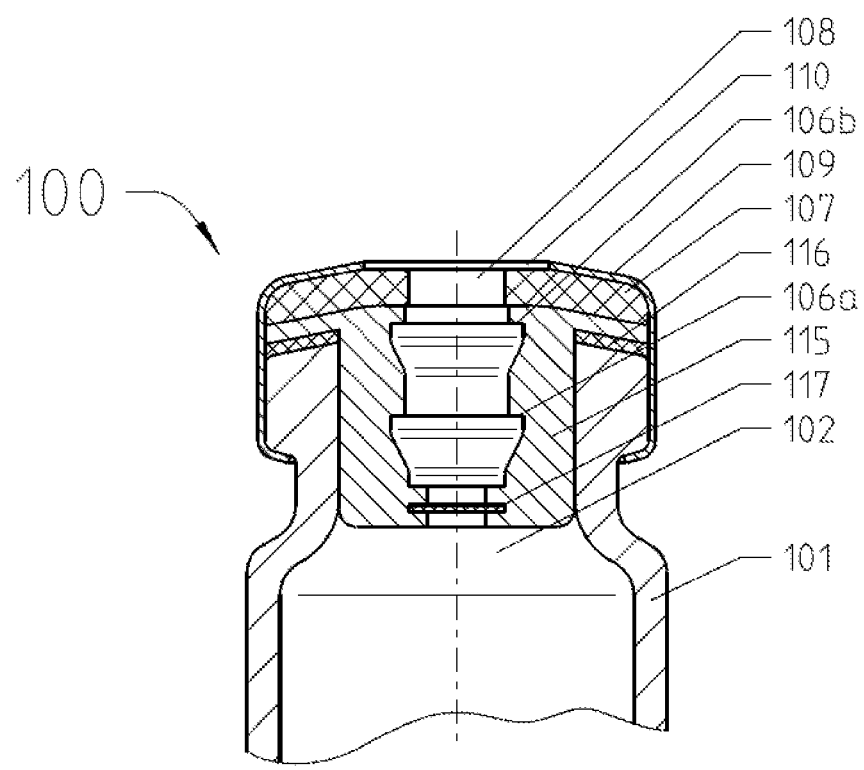
FIG. 6A is a sectional view of the distal end of an assembled cartridge according to a third embodiment of the present invention with a vented closure system.
Figure 6B:
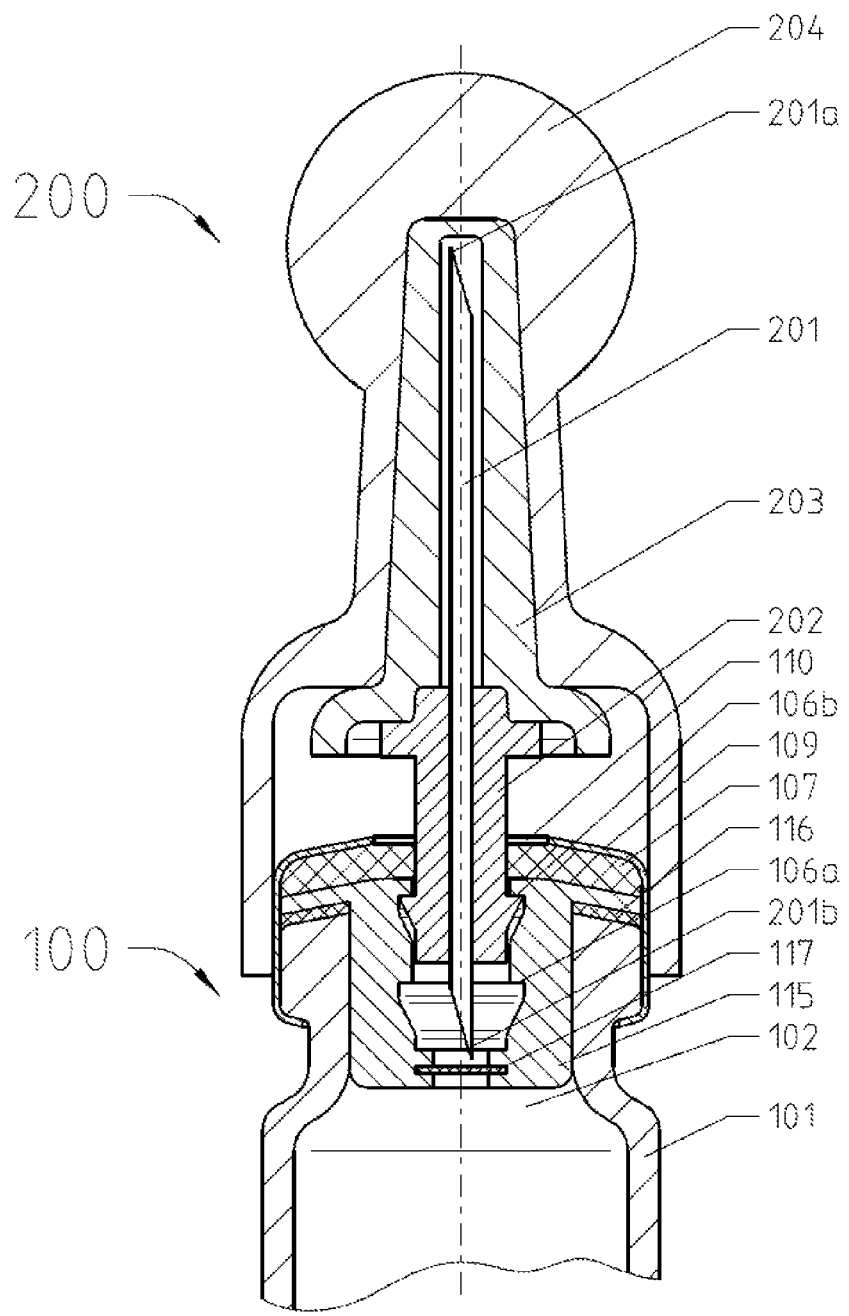
FIG. 6B is a sectional view of the distal end of the cartridge of FIG. 6A with an attached needle system.

As a first step in the closing process of cartridges, the pre-assembled vented housing insert assembly 118 is inserted into the distal open end 102, thereby sealing the cartridge barrel 101. By a crimping step the closure system is fixed to the cartridge barrel 101 (FIG. 6A). Secondly, the pre-assembled needle system 200 is attached to the closure system and positioned in the first inactive position, where the semi-permeable membrane 117 is not pierced by the proximal needle tip 201b (FIG. 6B). In this example the inner needle cap 203 would be manufactured in a rubber material, and would seal against the preferably overmolded needle hub 202, in order to maintain the sterility of the needle.

The assembly of the individual parts of the closure system does not need to be completely performed during the manufacturing process of the product. The closure system can also be provided partially pre-assembled. Pre-assembly may be performed as describes above with respect to examples 1 to 4.

FIG. 6C shows the closure system in a venting position. The outer needle cover 204 and the inner needle cap 203 are removed from the system and the needle is still locked in the inactive position without piercing the semi-permeable membrane 117. Advancing the plunger allows air entrapped in the cartridge to pass the gas-permeable membrane 117 and escape through the needle 201. In this position, the injection system can be vented ("priming step") to remove air from the system prior to injection.

Figure 6D:
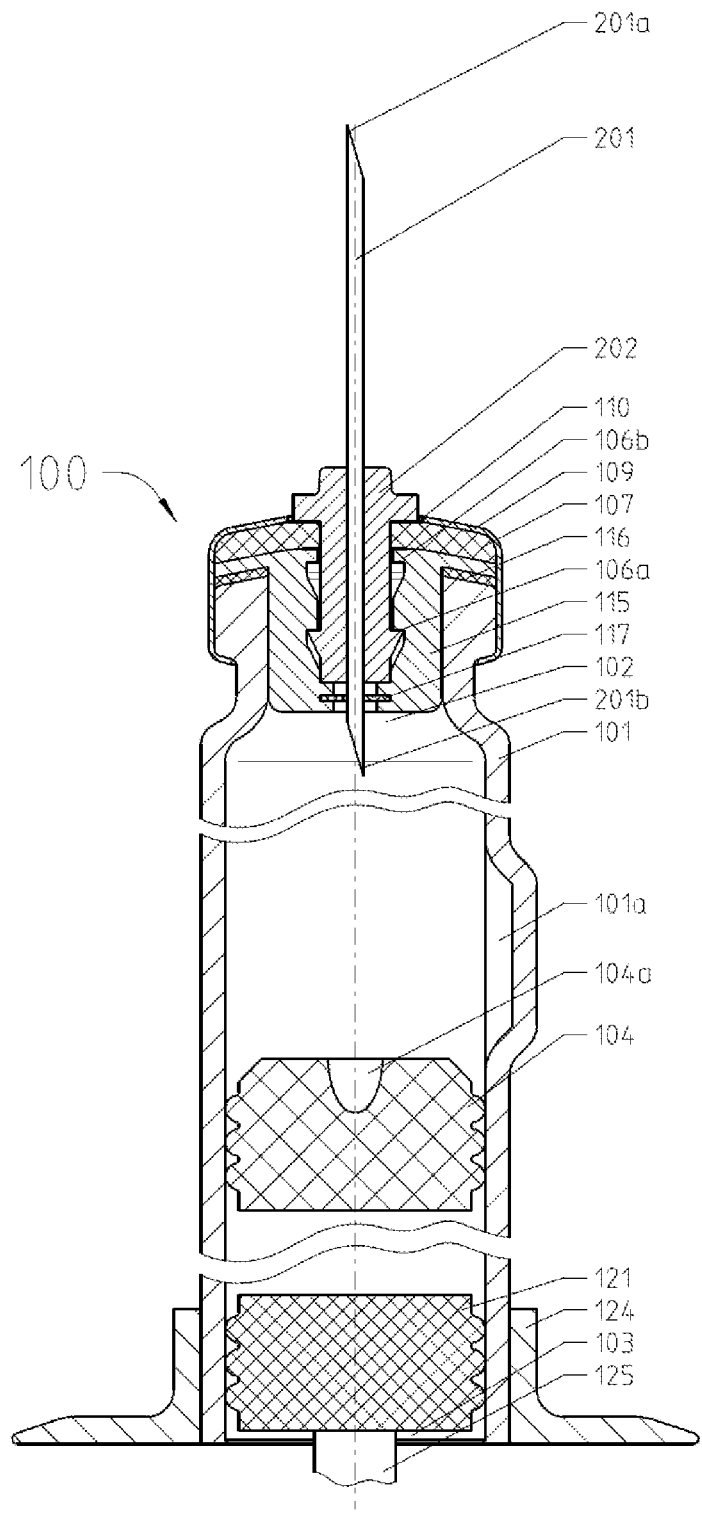
FIG. 6D is a schematic view of the distal end of the cartridge of FIG. 6A with an activated needle system needle, assembled as a ready-to-use syringe.

To allow injection, the system is activated by further pushing the needle system 200 into the vented housing insert 115. The mating features 202a of the needle hub 202 disengage from the distal mating features 106b of the vented housing insert 115 and engage with the proximal mating features 106a. FIG. 6D shows the cartridge system locked in activated needle position. Upon activation, the proximal needle tip 201b penetrates the semi-permeable membrane 117 and the needle is locked into position and cannot return to the first, inactive, inserted position. FIG. 6D illustrates the closure system as part of a dual chamber syringe with a finger rest 124 in activated needle position.

Figure 6E:
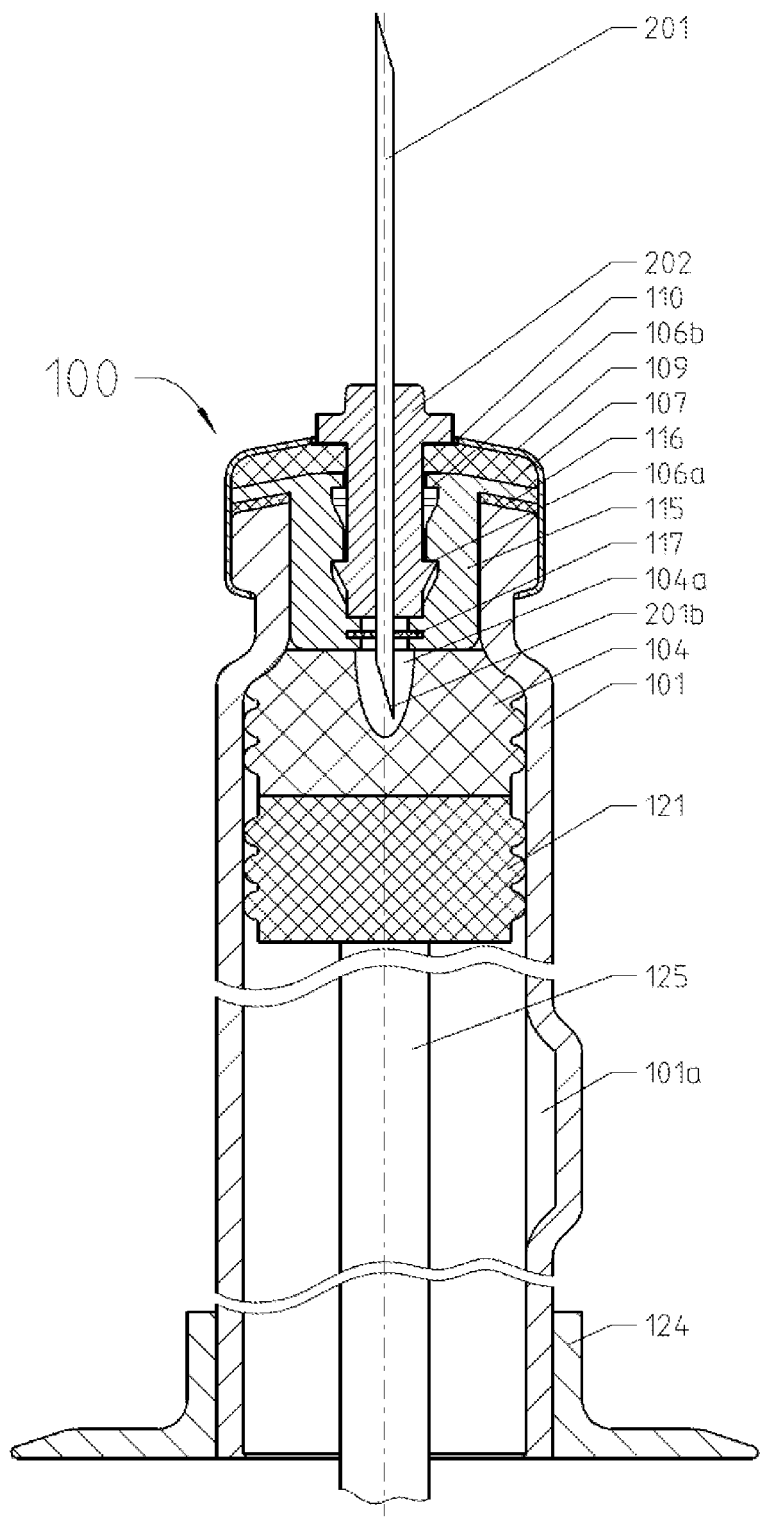
FIG. 6E is a schematic view of the cartridge of FIG. 6D after withdrawal of contents.

FIG. 6E shows the cartridge system after withdrawal of the contents. The conical piston 104 with the in-molded needle cavity 104a is shaped such that at contact of the piston 104 with the housing insert 115 the dead space in between is reduced to the volume of the needle cavity 104a.

An advantage of the proposed integrated needle is that the number of handling steps for the user is reduced, making the overall device system easier and more convenient to use. Furthermore, the risk of causing damage to the needle, such as blockage or bending of the needle, or damage to the cartridge seal, in this embodiment the semi-permeable membrane 117, during manual attachment of a separate needle is eliminated. In addition, the integrated needle of example 5 shares the same advantages as example 2 and example 4 with respect to keeping powder away from the pre-attached needle and preventing possible needle blockage. Furthermore the integrated needle of example 5 is activated in the same manner as the integrated needles of example 2 and example 4. Therefore, the same potential exists for automation of needle activation by the device mechanism.

A further advantage of example 5 is that the rubber sealing face of rubber stopper 105 has been replaced with a semi-permeable membrane 117. The material of the semi-permeable membrane is designed to permit the permeation of gases, but prevent the transmission of liquid. After mixing of powder and diluent in a dual chamber cartridge there is normally a volume of gas that is preferably expelled prior to delivery of the injection. Once the inner needle cap 203 is removed the semi-permeable membrane 117 now permits the gas to be purged from the cartridge barrel 101 without the loss of any liquid. Therefore, the dose accuracy of the injection is not compromised by the gas priming process.

Figure 7A:
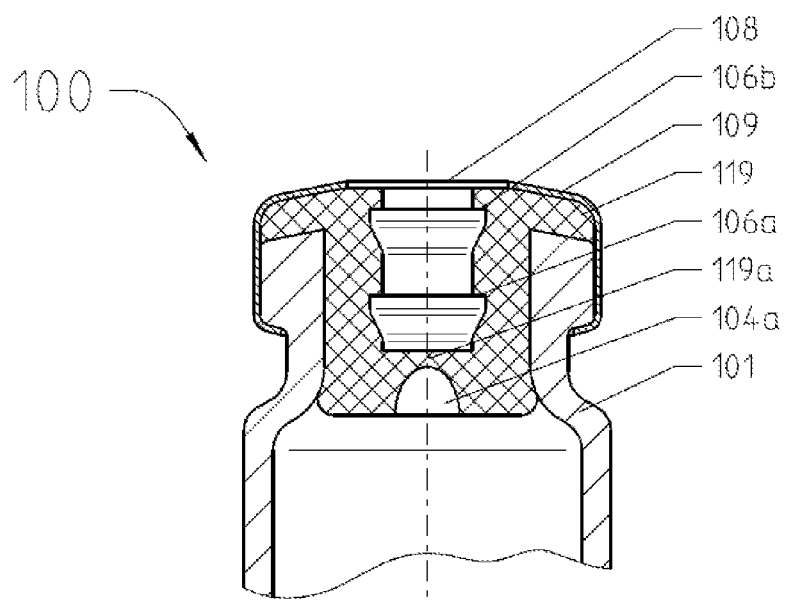
FIG. 7A is a sectional view of the distal end of an assembled cartridge according to a fourth embodiment of the present invention with a one-piece closure system.
Figure 7C:
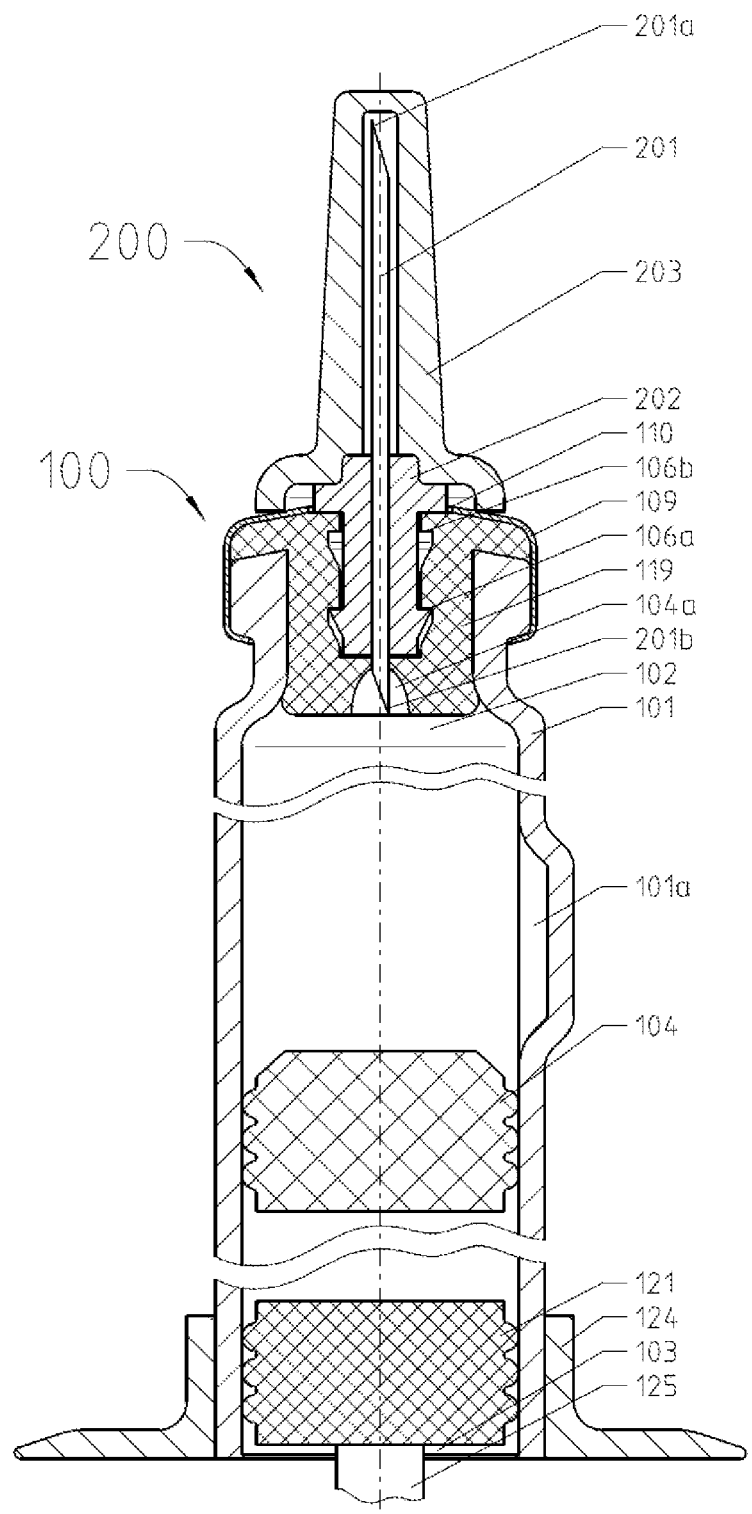
FIG. 7C is a schematic view of the cartridge of FIG. 7A with an activated needle system needle, assembled as a ready-to-use syringe.

Referring to FIG. 7A to 7C, there is illustrated an exemplary assembled one-piece closure system for a cartridge according to the invention. The closure system, generally referenced with the number 100, includes a cartridge barrel 101 which has a distal open end 102 and a proximal open end 103, opposite to the open end 102. The proximal open end 103 is closed by a piston 104 (piston not shown; cp. prior examples). The distal open end 102 is closed by a one-piece rubber insert 119 with in-molded needle cavity 104a. The one-piece insert 119 is fixed to the cartridge barrel 101 by crimping of an aluminum cap 109. The aluminum cap 109 has a central opening 110 that allows access to the inner void space 111 of the one-piece insert 106. The preferred embodiment of example 6 has attached a pre-assembled needle system 200 to the closure system 100. Thus, a film seal 112 is not required as the inner void space 111 is protected against contamination by an interference fit between the inserted needle system 200 and the housing insert 106.

As a first step in the closing process of cartridges, the one-piece insert assembly is inserted into the distal open end 102, thereby sealing the cartridge barrel 101. By a crimping step the closure system is fixed to the cartridge barrel 101 (FIG. 7A). Secondly, the pre-assembled needle system 200 is attached to the closure system and positioned in the first inactive position, where the rubber septum 119a is not pierced by the proximal needle tip 201b (FIG. 7B). In this example the inner needle cap 203 would be manufactured in a rubber material, and would seal against the needle hub 202, in order to maintain the sterility of the needle.

The assembly of the individual parts of the closure system does not need to be completely performed during the manufacturing process of the product. The closure system can also be provided partially pre-assembled as described above.

To allow injection, the system is activated by further pushing the needle system 200 into the one-piece insert 119. The mating features 202a of the needle hub 202 disengage from the distal mating features 106b of the housing insert 119 and engage with the proximal mating features 106a. FIG. 7C shows the cartridge system locked in activated needle position. Upon activation, the proximal needle tip 201b penetrates the rubber septum 119a and the needle is locked into position such that it cannot return to the first, inactive, insertion position and where it cannot be removed from the one-piece insert 119. Then, the needle housing 204 is removed, still leaving the distal needle tip 201a being protected by the inner needle cap 203. Shortly before injection, the inner needle cap 203 is removed and the injection system is ready for injection. The inner needle cap 203 may alternatively be combined with or adhered to the outer needle cover 204 and therefore both outer needle cover 204 and inner needle cover 203 are removed in a single user action.

An advantage of the proposed integrated needle is that the number of handling steps for the user is reduced, making the overall device system easier and more convenient to use. Furthermore, the risk of causing damage to the needle, such as blockage or bending of the needle, or damage to the cartridge seal during manual attachment of a separate needle is eliminated.

The integrated needle of example 6 shares the same advantages as examples 2, 4 and 5 with respect to keeping powder away from the pre-attached needle and preventing possible needle blockage. Furthermore the integrated needle of example 6 is activated in the same manner as the integrated needles of examples 2, 4 and 6. Therefore, the same potential exists for automation of needle activation by the device mechanism.

The invention claimed is:

1. An Injection cartridge configured for assembly within a cartridge holder component of an injection device, where the injection cartridge comprises
   a) a barrel having a distal end and a proximal end;
   b) a housing insert at least partially received in the distal end of the barrel and having a proximal end and a distal end extending beyond the distal end of the barrel;
   c) a central opening in the housing insert configured for at least partially receiving a removable tamper-proof plug having a hub configured to prevent contamination of the central opening or a needle assembly comprising a needle with a distal tip, a proximal tip and a hub surrounding the needle;
   d) at least two snap fit connectors within the central opening of the housing insert configured to guide, align and hold the hub in at least two axial positions within the central opening;
   e) a rubber sealing disc having a distal end and a central opening, where the rubber sealing disc covers the distal end of the housing insert such that the two central openings are aligned; and
   f) a metal cap having a hole to allow access to the two central openings, where the cap covers the distal ends of the rubber sealing disc and housing insert and is crimped on the distal end of the barrel to hold the housing insert within the barrel such that no part of the housing insert protrudes outside the metal cap,
   wherein the injection cartridge is configured to fit completely within a cartridge holder of an injection device.

2. The injection cartridge according to claim 1, characterized in that the central opening of the housing insert has a cylindrical inner surface for guiding a cylindrical outer surface of the hub or a conical inner surface for guiding a conical outer surface of the hub.

3. The injection cartridge according to claim 1, characterized in that at least one snap fit of the central opening of the housing insert has an inner surface and that the hub has an outer surface with at least one protrusion being provided on one of said inner or outer surfaces, and at least one recess being provided on the other of said inner or outer surface or surfaces for retaining the tamper-proof plug or needle system in the housing insert.

4. The injection cartridge according to claim 3, characterized in that there are provided two recesses in one of said inner or outer surfaces which are spaced apart in an axial direction of the barrel for retaining the tamper-proof plug or the needle system in two different axial positions in the housing insert.

5. The injection cartridge according to claim 1, characterized in that the barrel has at its distal end a neck portion with a reduced inner diameter with the housing insert being at least partially received in said neck portion.

6. The injection cartridge according to claim 1, characterized in that the central opening of the housing insert is a through-hole being provided with closing means for blocking a fluid communication between the barrel and the central opening.

7. The injection cartridge according to claim 6, characterized in that the closing means comprises a separate stopper member, a semi-permeable membrane attached to the housing insert or a septum being integrally formed with the housing insert.

8. The injection cartridge according to claim 1, characterized in that the hub surrounds the needle near its proximal tip.

9. The injection cartridge according to claim 1, characterized in that the distal end of the barrel is closed by a stopper member and the proximal end of the barrel is closed by a piston displaceable in said barrel such that the barrel, the stopper member and the piston define at least one chamber containing at least one product.

10. The injection cartridge according to claim 1, characterized in that the barrel is a dual-chamber container with the distal end of the barrel being closed by a stopper member, the proximal end of the barrel being closed by a proximal piston displaceable in said barrel and with a further displaceable piston being provided between the stopper member and the first piston such that the barrel, the stopper member and the pistons define two chambers each containing at least one product.

11. The injection cartridge according to claim 10, characterized in that the barrel is provided with a bypass being arranged such that a first product being received in a first chamber is allowed to flow into the second chamber bypassing the further piston.

12. The injection cartridge according to claim 1, characterized in that in a piston, in the housing insert and/or in a stopper member there is provided a needle cavity for receiving the proximal tip.

13. The injection cartridge according to claim 1, characterized in that the housing insert and/or stopper member has a cup-like configuration and is provided with a radial flange covering the distal front wall of the barrel.

14. The injection cartridge according to claim 1, characterized in that the cartridge contains a medicament selected from human insulin or a human insulin analogue or derivative, glucagon-like peptide (GLP-1) or an analogue or derivative thereof, or exedin-3 or exedin-4 or an analogue or derivative of exedin-3 or exedin-4, or a hypophysis hormone or a hypothalamus hormone or a regulatory active peptide or an antagonist of said hormones.

15. A needle system, especially for an injection cartridge according to claim 1, the needle system comprising a needle with a distal tip extending distally beyond the distal end of the barrel, a proximal tip and a hub surrounding the needle near its proximal tip wherein the hub is provided with attachment means for guiding and retaining the hub in the injection cartridge.

16. The needle system according to claim 15, characterized in that at least one of the snap fit connectors comprises at least one flange-like protrusion provided on a cylindrical outer surface of the hub.

17. A combination of an injection cartridge according to claim 1, characterized in that the configuration of the central opening of the housing insert of the cartridge and the configuration of the hub are adapted to each other such that the needle of the needle system is centered and guided to lie essentially within the longitudinal axis of the barrel.

18. The injection cartridge of claim 1 further comprising a film seal attached to the metal cap and covering the two central openings to protect the central opening of the housing insert from contamination.

19. The injection cartridge of claim 1 further comprising a removable tamper-proof plug comprising a hub that is at least partially positioned in the central opening of the housing insert and is configured for removal prior to a first use of the injection cartridge, the tamper-proof plug further configured to allow the plug to be re-positioned within the central opening of the housing insert upon after final use of the injection cartridge and where the hub has at least one of snap fit connector comprising at least one flange-like protrusion provided on a cylindrical outer surface of the hub.

20. An Injection cartridge configured for assembly within a cartridge holder component of an injection device, where the injection cartridge comprises a barrel having a distal end and a proximal end and a housing insert, wherein the housing insert is at least partially received in the distal end of the barrel and wherein the housing insert comprises a central opening for at least partially receiving a needle system comprising a needle with a distal tip, a proximal tip and a hub surrounding the needle, with said central opening comprising retaining means for guiding and retaining the hub and being aligned to attachment means of the hub and wherein the housing insert is provided with a flange having a sleeve-like section encompassing the distal end of the barrel wherein the sleeve-like section has at least one radial protrusion for fixing the cartridge in the cartridge holder.

* * * * *

UNITED STATES PATENT AND TRADEMARK OFFICE
CERTIFICATE OF CORRECTION

PATENT NO. : 8,574,214 B2  Page 1 of 1
APPLICATION NO. : 13/056160
DATED : November 5, 2013
INVENTOR(S) : Kühn et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 151 days.

Signed and Sealed this
Twenty-second Day of September, 2015

Michelle K. Lee
*Director of the United States Patent and Trademark Office*